US012582667B2

(12) United States Patent
Tavazoie et al.

(10) Patent No.: US 12,582,667 B2
(45) Date of Patent: Mar. 24, 2026

(54) COMPOSITIONS AND METHODS TO TREAT METASTATIC GASTROINTESTINAL CANCER

(71) Applicant: The Rockefeller University, New York, NY (US)

(72) Inventors: Sohail Tavazoie, New York, NY (US); Norihiro Yamaguchi, New York, NY (US); Kivanc Birsoy, New York, NY (US)

(73) Assignee: The Rockefeller University, New York, NY (US)

( * ) Notice: Subject to any disclaimer, the term of this patent is extended or adjusted under 35 U.S.C. 154(b) by 961 days.

(21) Appl. No.: 17/762,529

(22) PCT Filed: Sep. 25, 2020

(86) PCT No.: PCT/US2020/052721

§ 371 (c)(1),
(2) Date: Mar. 22, 2022

(87) PCT Pub. No.: WO2021/062157

PCT Pub. Date: Apr. 1, 2021

(65) Prior Publication Data

US 2022/0339184 A1 Oct. 27, 2022

Related U.S. Application Data

(60) Provisional application No. 62/907,113, filed on Sep. 27, 2019.

(51) Int. Cl.

| | |
|---|---|
| ***A61P 35/00*** | (2006.01) |
| ***A61K 31/00*** | (2006.01) |
| ***A61K 31/7105*** | (2006.01) |
| ***A61K 38/00*** | (2006.01) |
| ***A61N 5/00*** | (2006.01) |

(52) U.S. Cl.

CPC ........ *A61K 31/7105* (2013.01); *A61K 38/005* (2013.01); *A61N 5/00* (2013.01); *A61P 35/00* (2018.01)

(58) Field of Classification Search

CPC ................................ A61P 35/00; A61K 31/00

See application file for complete search history.

(56) References Cited

U.S. PATENT DOCUMENTS

| | | | |
|---|---|---|---|
| 2011/0206614 A1 | 8/2011 | McAllister et al. | |
| 2015/0240235 A1 | 8/2015 | Collombat et al. | |
| 2017/0050924 A1 * | 2/2017 | Martinez et al. | ..... C07C 279/14 |

FOREIGN PATENT DOCUMENTS

| | | |
|---|---|---|
| WO | 2004/096235 A2 | 11/2004 |
| WO | 2008/127291 A2 | 10/2008 |
| WO | 2014/028461 A2 | 2/2014 |
| WO | 2018136009 A1 | 7/2018 |
| WO | 2019/197683 A1 | 10/2019 |

OTHER PUBLICATIONS

Kurth et al. (2021) "Therapeutic targeting of SLC6A8 creatine transporter suppresses colon cancer progression and modulates human creatine levels" Sci Adv, 7 : eabi7511, 13 pages. (Year: 2021).*

Kurth et al. (2021) "Therapeutic targeting of SLC6A8 creatine transporter inhibits KRAS mutant and wildtype colon cancer and modulates human creatine levels" bioRxiv preprint, 44 pages. (Year: 2021).*

International Search Report and Written Opinion mailed Jan. 13, 2021 issued in International Application PCT/US2020/052721, 15 pages.

Supplementary European Search Report issued Nov. 3, 2023 is related European Patent Application No. 20869291.3, 12 pgs.

* cited by examiner

*Primary Examiner* — James Joseph Graber

(74) *Attorney, Agent, or Firm* — Fox Rothschild LLP

(57) ABSTRACT

The present invention relates to agents and methods for treating gastrointestinal cancer (e.g., metastatic colorectal cancer) in a subject in need thereof. The method includes suppressing the enzymatic activity of DHODH and/or decreasing the level of creatine via suppression of creatine transporter channel SLC6a8 in the subject. In some embodiments, the suppression step can be carried out by administering to the subject a set of small molecule compounds.

32 Claims, 6 Drawing Sheets

Specification includes a Sequence Listing.

A

B

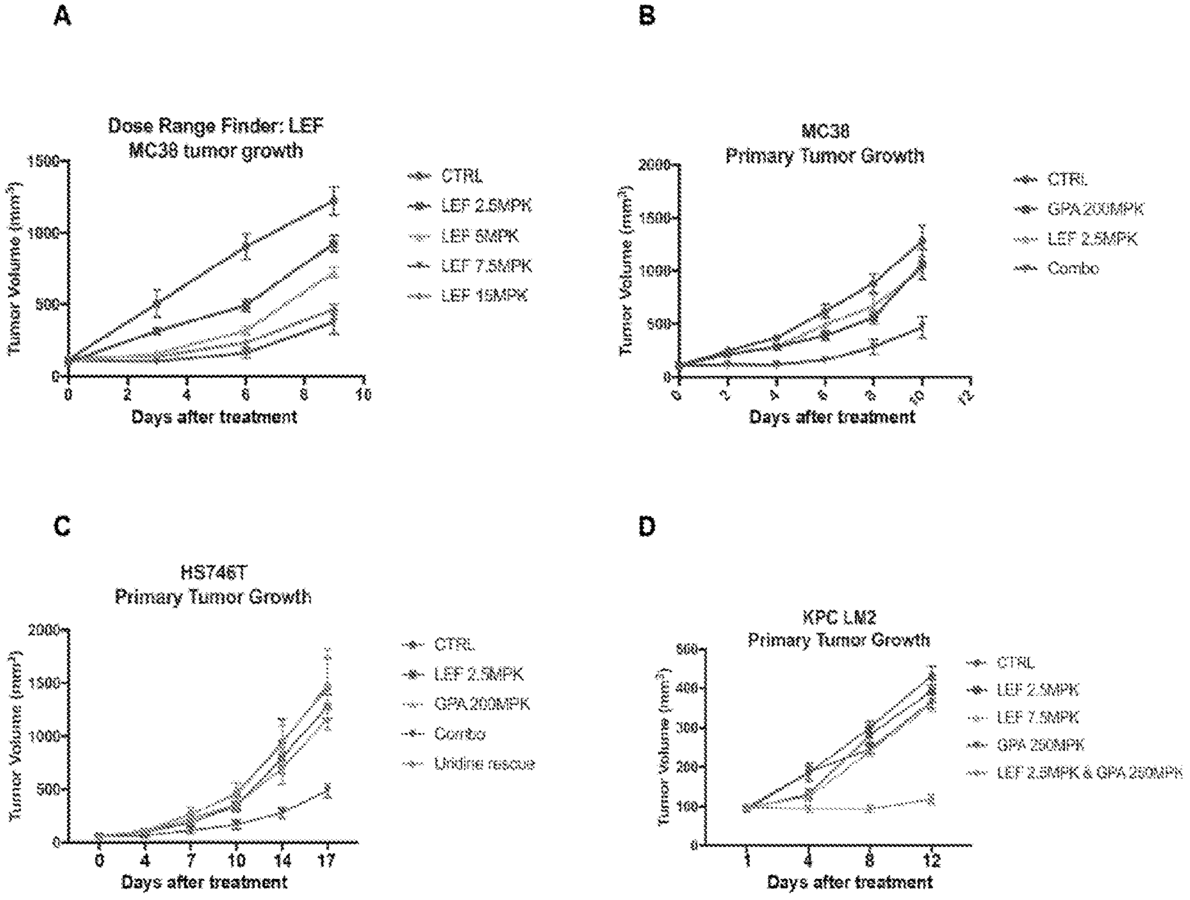
FIGS. 4A, 4B, 4C, and 4D

SEQUENCE LISTING

```
<160> NUMBER OF SEQ ID NOS: 10

<210> SEQ ID NO 1
<211> LENGTH: 19
<212> TYPE: DNA
<213> ORGANISM: artificial
<220> FEATURE:
<223> OTHER INFORMATION: synthetic

<400> SEQUENCE: 1

aaggtgttcc cattgaagg                                                   19


<210> SEQ ID NO 2
<211> LENGTH: 20
<212> TYPE: DNA
<213> ORGANISM: artificial
<220> FEATURE:
<223> OTHER INFORMATION: synthetic

<400> SEQUENCE: 2

gaagttgtag ccaaagaagg                                                  20


<210> SEQ ID NO 3
<211> LENGTH: 20
<212> TYPE: DNA
<213> ORGANISM: artificial
<220> FEATURE:
<223> OTHER INFORMATION: synthetic

<400> SEQUENCE: 3

gaccagtcaa caggggacat                                                  20


<210> SEQ ID NO 4
<211> LENGTH: 20
<212> TYPE: DNA
<213> ORGANISM: artificial
<220> FEATURE:
<223> OTHER INFORMATION: synthetic

<400> SEQUENCE: 4

cctgaccaag gaaagcaaag                                                  20


<210> SEQ ID NO 5
<211> LENGTH: 21
<212> TYPE: DNA
<213> ORGANISM: artificial
<220> FEATURE:
<223> OTHER INFORMATION: synthetic

<400> SEQUENCE: 5

ctgcataacg gtctggactt c                                                21


<210> SEQ ID NO 6
<211> LENGTH: 19
<212> TYPE: DNA
<213> ORGANISM: artificial
<220> FEATURE:
```

-continued

```
<223> OTHER INFORMATION: synthetic

<400> SEQUENCE: 6

cagcaactgc ccgtactcc                                                  19


<210> SEQ ID NO 7
<211> LENGTH: 20
<212> TYPE: DNA
<213> ORGANISM: artificial
<220> FEATURE:
<223> OTHER INFORMATION: synthetic

<400> SEQUENCE: 7

ggctgtattc ccctccatcg                                                 20


<210> SEQ ID NO 8
<211> LENGTH: 22
<212> TYPE: DNA
<213> ORGANISM: artificial
<220> FEATURE:
<223> OTHER INFORMATION: synthetic

<400> SEQUENCE: 8

ccagttggta acaatgccat gt                                              22


<210> SEQ ID NO 9
<211> LENGTH: 20
<212> TYPE: DNA
<213> ORGANISM: artificial
<220> FEATURE:
<223> OTHER INFORMATION: synthetic

<400> SEQUENCE: 9

ccacgggaga tgagcgtttc                                                 20


<210> SEQ ID NO 10
<211> LENGTH: 19
<212> TYPE: DNA
<213> ORGANISM: artificial
<220> FEATURE:
<223> OTHER INFORMATION: synthetic

<400> SEQUENCE: 10

cagggaggtg aagcgaaca                                                  19
```

COMPOSITIONS AND METHODS TO TREAT METASTATIC GASTROINTESTINAL CANCER

CROSS-REFERENCE TO RELATED APPLICATIONS

The present application is a National Stage Application under 35 U.S.C. § 371 of International Application No. PCT/US2020/052721 filed Sep. 25, 2020, which claims priority under 35 U.S.C. § 119(e) to U.S. Provisional Patent Application No. 62/907,113, filed Sep. 27, 2019. The foregoing applications are incorporated by reference herein.

STATEMENT REGARDING FEDERALLY SPONSORED RESEARCH

The invention disclosed herein was made, at least in part, with government support under Grant No. 1DP2OD006506-01 from the National Institutes of Health. Accordingly, the U.S. Government has certain rights in this invention.

FIELD OF THE INVENTION

This invention relates to agents and methods for treatment of gastrointestinal cancer.

BACKGROUND OF THE INVENTION

Cancer is among the leading causes of death worldwide. There were 18 million new cases and 9 million mortality in 2018 worldwide. 90% of cancer-related mortality is from metastatic cancer. For example, the 5-year survival rate of colorectal cancer patients with early local disease is >90%, but it drops to 7% in patients with distant organ metastasis. Although it has become standard treatment to administer chemotherapeutics to patients with a higher likelihood of post-surgically developing metastatic disease, a subset of cancer cells in the patients being treated with the post-surgical chemotherapy will eventually develop resistance to 5-FU, the key compound of the current standard treatment, and evolve as metastatic cancer.

Colorectal cancer (CRC) is a major cause of human death. Mortality is primarily due to metastatic organ colonization, with liver being the primary organ affected. CRC remains a challenging disease despite multiple advances over the last six decades. Some patients with metastatic CRC can experience regression responses to current therapies, though most succumb to their disease within three years.

Thus, there remains a pressing need for novel methods and therapeutic agents to suppress distant organ metastasis.

SUMMARY OF THE INVENTION

This disclosure addresses the above-mentioned need by providing agents and methods for suppressing cancer metastasis. In one aspect, the invention features a method for treating gastrointestinal cancer (e.g., metastatic colorectal cancer) in a subject in need thereof. The method includes suppressing the enzymatic activity of DHODH and/or decreasing the level of creatine via suppression of creatine transporter channel SLC6a8 in the subject.

In some embodiments, the suppression step can be carried out by administering to the subject a set of small molecule compounds. For example, the suppression step can be carried out by administering to the subject a DHODH inhibitor, such as leflunomide. Other examples of DHODH inhibitors include, without limitation, atovaquone, brequinar sodium, teriflunomide, BAY-2402234, and AG-636.

In some embodiments, the decreasing step can be carried out by administering to the subject beta-guanidinopropionic acid (β-GPA), or a pharmaceutically acceptable salt thereof.

In another aspect, also provided is a method for treating metastatic gastrointestinal cancers in a subject in need thereof. The method includes administering compounds to the subject an effective amount of a DHODH inhibitor, or a pharmaceutically acceptable salt thereof, and an effective amount of a β-GPA, or a pharmaceutically acceptable salt thereof, to suppress metastatic colonization of gastrointestinal cancer. In some embodiments, the DHODH inhibitor can be any one of: atovaquone, brequinar sodium, leflunomide, teriflunomide, BAY-2402234, AG-636, and a combination thereof.

In another aspect, also provided is a method for treating cancer (e.g., metastatic cancers) in a subject in need thereof. The method includes administering to the subject an effective amount of a DHODH inhibitor (e.g., atovaquone, brequinar sodium, leflunomide, teriflunomide, BAY-2402234, AG-636, or a combination thereof), or a pharmaceutically acceptable salt thereof, and β-GPA, or a pharmaceutically acceptable salt thereof. In some embodiments, the effective amount is an amount of the DHODH inhibitor and β-GPA, or a pharmaceutically acceptable salt thereof that is together effective to suppress metastatic progression (e.g., metastatic colonization) of the cancer. In some embodiments, the DHODH inhibitor is leflunomide. In some embodiments, the cancer is gastrointestinal cancer, such as colorectal cancer, esophageal cancer, or gastric cancer, pancreatic cancer, liver cancer, breast cancer, prostate cancer, lung cancer, and melanoma. In some embodiments, the cancer is gastrointestinal cancer. In some embodiments, the cancer is lung cancer. In some embodiments, the effective amount is an amount effective to suppress metastatic colonization of the cancer to the liver and/or brain.

In some embodiments, the DHODH inhibitor or the pharmaceutically acceptable salt thereof and/or β-GPA or the pharmaceutically acceptable salt thereof are administered to the subject intratumorally, intravenously, subcutaneously, intraosseously, orally, transdermally, in sustained release, in controlled release, in delayed release, as a suppository, or sublingually.

In some embodiments, the DHODH inhibitor or the pharmaceutically acceptable salt thereof is administered to the subject before (e.g., at least one day before, at least one week before, at least one month before), after (e.g., at least one day after, at least one week after, at least one month after), or concurrently with the β-GPA or the pharmaceutically acceptable salt thereof.

In some embodiments, the DHODH inhibitor or the pharmaceutically acceptable salt thereof and the β-GPA or the pharmaceutically acceptable salt thereof are provided in a single composition. Alternatively, the DHODH inhibitor or the pharmaceutically acceptable salt thereof and the β-GPA or the pharmaceutically acceptable salt thereof can be provided in separate compositions.

In some embodiments, the method further comprises administering to the subject an additional anti-cancer therapy (e.g., surgery, radiation therapy, and/or one or more therapeutic agents, such as an anti-tumor or anti-cancer agent (e.g., irinotecan, oxaliplatin, cetuximab, avastin, leucovorin, and/or 5-fluorouracil (5-FU)). In some embodiments, the subject has previously been administered at least one prior anti-cancer therapy (e.g., surgery, radiation therapy, and/or one or more therapeutic agents, such as an anti-tumor or anti-cancer agent). In some embodiments, the therapeutic agent is cyclocreatine, an RNAi agent, a nucleic acid, a vector, 5-FU, Oxaliplatin, irinotecan, oxaliplatin, capecitabine, gemcitabine, cetuximab, taxol, avastin, folinic acid (leucovorin), regorafenib, zaltrap, topoisomerase I inhibitors, etirinotecan pegol, tivantinib, sonolisib, sorafenib, linifanib, kinase inhibitors, telatinib, XL281 (BMS-908662), robatumumab, IGF1-R inhibitors, or combinations thereof.

This disclosure further provides a method for treating colorectal cancer, gastric cancer, esophageal cancer, or pancreatic cancer in a subject in need thereof. In some embodiments, the cancer is cholangial cancer.

In some embodiments, the cancer expresses creatine kinase brain-type (CKB) (e.g., the cancer cells express CKB). In some embodiments, the cancer has been determined to express CKB based on histological examination of a tissue sample from the subject. In some embodiments, the subject has been identified as likely to respond to treatment with a DHODH inhibitor and β-GPA, or a pharmaceutically acceptable salt thereof (e.g., based on histological examination of a tissue sample from the subject to determine the level of CKB expression).

In some embodiments, the cancer expresses SLC6a8 (e.g., the cancer cells express SLC6a8). In some embodiments, the cancer has been determined to express SLC6a8 based on histological examination of a tissue sample from the subject. In some embodiments, the subject has been identified as likely to respond to treatment with a DHODH inhibitor and β-GPA, or a pharmaceutically acceptable salt thereof (e.g., based on histological examination of a tissue sample from the subject to determine the level of SLC6a8 expression)

This disclosure additionally provides a method comprising suppressing metastatic colonization of lung cancer in the liver of a subject in need thereof.

In another aspect, the invention provides a pharmaceutical composition comprising (i) an effective amount of a dihydroorotate dehydrogenase (DHODH) inhibitor, or a pharmaceutically acceptable salt thereof, (ii) an effective amount of a beta-guanidinopropionic acid (β-GPA), or a pharmaceutically acceptable salt thereof, and (iii) pharmaceutically acceptable carrier. The invention also provides a kit comprising (i) an effective amount of a dihydroorotate dehydrogenase (DHODH) inhibitor, or a pharmaceutically acceptable salt thereof, and (ii) an effective amount of a beta-guanidinopropionic acid (β-GPA), or a pharmaceutically acceptable salt thereof. The pharmaceutical composition or the kit can further comprise an additional therapeutic agent described above.

In a further aspect, the invention provides a method for evaluating a clinical survival outcome of a subject having a cancer. The method comprises obtaining from the subject a sample containing cancer cells; grafting the sample into a non-human animal (such as a mouse); maintaining the animal for a period of time to allow the grafted cancer cells to form a tumor; determining a growth level, an engraft level, or a metastasis level of the tumor, and comparing one or more of the levels to a predetermined reference value.

In some embodiments of any of the foregoing methods, the DHODH inhibitor is atovaquone administered in an amount of 500 to 1500 mg per day, e.g., 500 mg once daily, 750 mg once daily, 1000 mg once daily, 1500 mg once daily, or 250 mg twice daily, 500 mg twice daily, or 750 mg twice daily.

In some embodiments of any of the foregoing methods, the DHODH inhibitor is leflunomide administered in an amount of 10 to 100 mg per day, e.g., 10 mg once daily, 20 mg once daily, or 100 mg once daily.

In some embodiments of any of the foregoing methods, the DHODH inhibitor is teriflunomide administered in an amount of 7 to 14 mg per day, e.g., 7 mg once daily, 14 mg once daily, or 7 mg twice daily.

In some embodiments of any of the foregoing methods, the β-GPA, or a pharmaceutically acceptable salt thereof, is administered in an amount of 0.01 to 100 mg/kg per day.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 2B is a close-up of the highlighted area of the diagram of FIG. 2A. Pyrimidine nucleotide precursors were up-regulated in the highly liver metastatic PDXs. Parental PDXs were used as references to the corresponding highly metastatic PDXs.

FIG. 3A shows that leflunomide inhibited liver metastatic colonization of Lvm3b cells. $1\times10^6$ Lvm3b cells were intrasplenically injected into athymic nude mice (n=4 per each cohort) on day 1, and leflunomide (7.5 mg/kg mouse body weight) or DMSO treatment was begun on day 1. The mice were imaged every week. Firefly luciferase bioluminescent images are shown ($p<0.0001$, Student's t-test). FIG. 3B shows a Kaplan-Meier plot of the experiment (n=4 per each cohort) (p=0.007, log-rank test).

FIGS. 4A, 4B, 4C, and 4D (collectively "FIG. 4") are a set of diagrams showing the combination of DHODH inhibition and SLC6a8 inhibition can be therapeutically exploited in gastrointestinal cancer models. FIG. 4A shows that 1 million MC38 cells were subcutaneously injected into C57BL/6 mice (n=4 per each cohort). Intraperitoneal leflunomide injection was started at the time that the average size of tumors reached 100 $mm^3$. The leflunomide treatment was given daily. MPK: mg/kg body weight of mouse. Tumor size was measured by a digital caliper, and tumor volume was calculated as volume=(the longest diameter of tumor/2)*(the shortest diameter of tumor). FIG. 4B shows that 1 million MC38 cells were subcutaneously injected to C57BL/6 mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of MC38 tumor (p=0.0004, Student t-test). FIG. 4C shows that 1 million HS746T cells were subcutaneously injected to NOD.Cg-Prkdc$^{scid}$ Il2rg$^{tm1Wjl}$/SzJ (Nod-Scid-Gamma; NSG) mice (n=4 per each cohort). Intraperitoneal leflunomide injection and oral β-GPA administration were started at the time that the average size of tumors reached to 100 $mm^3$. Leflunomide and β-GPA were given daily. Leflunomide/β-GPA combo treatment significantly reduced the growth of HS746T tumor (p=0.0045, Student t-test). Pyrimidine precursor nucleoside, uridine administration rescued the leflunomide-induced tumor growth reduction supporting the on-target efficacy of leflunomide. FIG. 4D shows that 1 million KPC LM2 cells were subcutaneously injected to C57BL/6 mice (n=4 per each cohort). Intraperitoneal leflunomide injection and oral β-GPA administration were started at the time that the average size of tumors reached to 100 $mm^3$. Leflunomide and β-GPA were given daily. Leflunomide/β-GPA combo treatment significantly reduced the growth of KPC LM2 tumor (p<0.0001, Student t-test).

FIG. 5A shows that 30 $mm^3$ fragments of the patient-derived tumor were surgically sutured into the subcutaneous tissue of athymic nude mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of CLR1 tumor (p=0.0011, Student t-test). FIG. 5B shows that 30 $mm^3$ fragments of patient-derived tumors were surgically sutured into the subcutaneous tissue of athymic nude mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of GAS HI tumor (p=0.008, Student t-test). Uridine administration rescued the leflunomide induced tumor growth suppression.

DETAILED DESCRIPTION OF THE INVENTION

Figure 1:
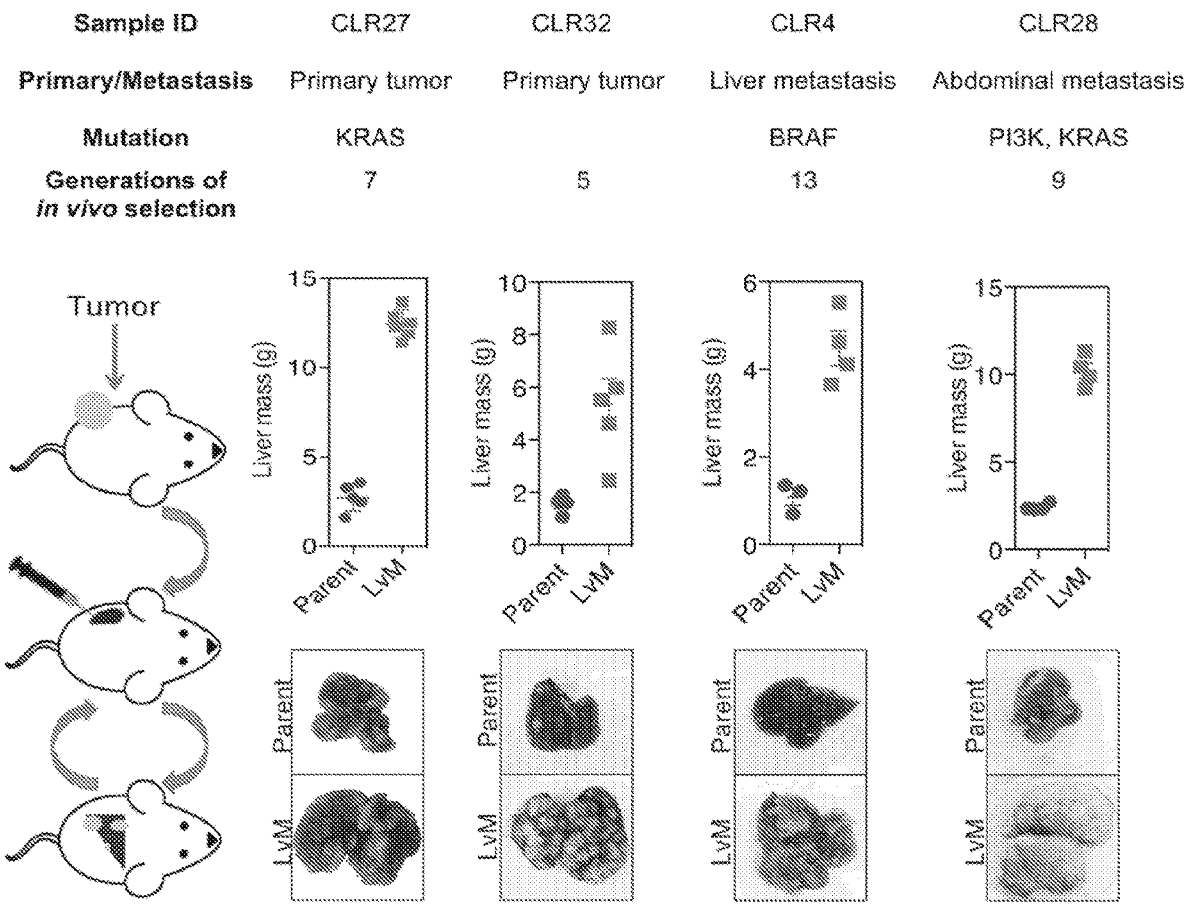
FIG. 1 is a set of diagrams and photographs showing in vivo selection that generates derivatives with enhanced ability to colonize mouse livers. In vivo selection was performed on four different CRC patient-derived primary and metastatic tumor xenograft (PDX) samples with varied anatomical locations and mutational backgrounds. The illustration on the left depicts the process used to generate the liver metastatic derivatives. Tumor samples from surgical specimens were inoculated subcutaneously into NSG mice. When the tumor reached the threshold size, it was removed from the mouse, dissociated into a single-cell suspension, and injected into the spleens of another set of mice as a means of introducing the colorectal cancer cells into the portal circulation. When the mice were deemed ill, the liver tumors were removed, dissociated, and re-injected to establish a next-generation liver derivative. This process was repeated numerous times (Range: 5-13) with each PDX sample to obtain a distant liver metastatic CRC PDX derivative requiring euthanasia of mice in 3 weeks after cancer cells injection. Each of the CRC PDX liver derivatives grew significantly faster in the livers compared to their parent samples.

This disclosure is based, at least in part, on unexpected discoveries that therapeutic inhibition of the pyrimidine biosynthetic enzyme DHODH with a DHODH inhibitor (e.g., leflunomide) substantially impaired CRC liver metastatic colonization and hypoxic survival.

Given that most colorectal cancer deaths occur as a result of complications of metastatic disease, a model that can predict which patients with advanced CRC harbor more aggressive disease could aid in appropriately positioning patients for experimental clinical trials and treatments. Accordingly, this disclosure also provides a colorectal cancer liver metastasis patient-derived xenograft model, as well as methods to identify candidate genes that may drive colorectal cancer liver colonization using this model. Also, metastatic CRC (mCRC) liver colonization was modeled using patient-derived primary and metastatic tumor xenografts (PDX). Such PDX modeling predicted patient survival outcomes. In vivo selection of multiple PDXs for enhanced metastatic capacity upregulated the gluconeogenic enzyme PCK1, which enhanced metastatic hypoxic survival by driving anabolic pyrimidine nucleotide biosynthesis. Consistently, highly metastatic tumors upregulated multiple pyrimidine biosynthesis intermediary metabolites. It was demonstrated in this disclosure that therapeutic inhibition of DHODH substantially diminished CRC liver metastatic colonization and hypoxic survival.

Thus, the present disclosure provides a mechanistic basis for the epidemiologic association of anti-gluconeogenic drugs with improved CRC metastasis outcomes, reveals the exploitation of a gluconeogenesis enzyme for pyrimidine biosynthesis during hypoxia, and implicates DHODH and PCK1 as metabolic therapeutic targets in colorectal cancer metastasis.

A. METHODS FOR TREATING GASTROINTESTINAL CANCER

This disclosure provides agents and methods for suppressing cancer metastasis. In one aspect, this disclosure provides a method for treating gastrointestinal cancer (e.g., metastatic colorectal cancer) in a subject in need thereof. The method includes suppressing the enzymatic activity of DHODH and/or decreasing the level of creatine via suppression of creatine transporter channel SLC6a8 in the subject.

In some embodiments, the enzymatic activity of DHODH can be suppressed by administering to the subject one or more DHODH inhibitors, or a pharmaceutically acceptable prodrug, a pharmaceutically active metabolite, a pharmaceutically acceptable salt thereof. For example, the suppression step can be carried out by administering to the subject a DHODH inhibitor, such as leflunomide. Other examples of DHODH inhibitors include, but are not limited to, atovaquone, brequinar sodium, teriflunomide, BAY-2402234, and AG-636.

In some embodiments, the level of creatine can be decreased by administering to the subject beta-guanidinopropionic acid (β-GPA), or a pharmaceutically acceptable prodrug, a pharmaceutically active metabolite, a pharmaceutically acceptable salt thereof.

In another aspect, also provided is a method for treating metastatic gastrointestinal cancers in a subject in need thereof. The method includes administering compounds to the subject an effective amount of a DHODH inhibitor, or a pharmaceutically acceptable salt thereof, and a β-GPA, or a pharmaceutically acceptable salt thereof, to suppress metastatic colonization of gastrointestinal cancer. In some embodiments, the DHODH inhibitor can be any one of atovaquone, brequinar sodium, leflunomide, teriflunomide, BAY-2402234, AG-636, and a combination thereof.

In another aspect, also provided is a method for treating cancer (e.g., metastatic cancers) in a subject in need thereof. The method includes administering to the subject an effective amount of a DHODH inhibitor (e.g., atovaquone, brequinar sodium, leflunomide, teriflunomide, BAY-2402234, AG-636, or a combination thereof), or a pharmaceutically acceptable salt thereof, and β-GPA, or a pharmaceutically acceptable salt thereof. In some embodiments, the effective amount is an amount of the DHODH inhibitor and β-GPA, or a pharmaceutically acceptable salt thereof that is together effective to suppress metastatic progression (e.g., metastatic colonization) of the cancer. In some embodiments, the DHODH inhibitor is leflunomide. In some embodiments, the cancer is gastrointestinal cancer, such as colorectal cancer, esophageal cancer, or gastric cancer, pancreatic cancer, liver cancer, breast cancer, prostate cancer, lung cancer, and melanoma. In some embodiments, the cancer is gastrointestinal cancer. In some embodiments, the cancer is lung cancer. In some embodiments, the effective amount is an amount effective to suppress metastatic colonization of the cancer to the liver and/or brain.

In some embodiments, the method further comprises administering to the subject an additional anti-cancer therapy (e.g., surgery, radiation therapy, and/or one or more therapeutic agents, such as an anti-tumor or anti-cancer agent (e.g., irinotecan, oxaliplatin, cetuximab, avastin, leucovorin, and/or 5-fluorouracil (5-FU)). In some embodiments, the subject has previously been administered at least one prior anticancer therapy (e.g., surgery, radiation therapy, and/or one or more therapeutic agents, such as an anti-tumor or anti-cancer agent). In some embodiments, the therapeutic agent is cyclocreatine, an RNAi agent, a nucleic acid, a vector, 5-FU, Oxaliplatin, irinotecan, oxaliplatin, capecitabine, gemcitabine, cetuximab, taxol, avastin, folinic acid (leucovorin), regorafenib, zaltrap, topoisomerase I inhibitors, etirinotecan pegol, tivantinib, sonolisib, sorafenib, linifanib, kinase inhibitors, telatinib, XL281 (BMS-908662), robatumumab, IGF1-R inhibitors, or combinations thereof.

In some embodiments of any of the foregoing methods, the DHODH inhibitor is atovaquone administered in an amount of 500 to 1500 mg per day, e.g., 500 mg once daily, 750 mg once daily, 1000 mg once daily, 1500 mg once daily, or 250 mg twice daily, 500 mg twice daily, or 750 mg twice daily.

In some embodiments of any of the foregoing methods, the DHODH inhibitor is leflunomide administered in an amount of 10 to 100 mg per day, e.g., 10 mg once daily, 20 mg once daily, or 100 mg once daily.

In some embodiments of any of the foregoing methods, the DHODH inhibitor is teriflunomide administered in an amount of 7 to 14 mg per day, e.g., 7 mg once daily, 14 mg once daily, or 7 mg twice daily.

In some embodiments of any of the foregoing methods, the β-GPA, or a pharmaceutically acceptable salt thereof, is administered in an amount of 0.01 to 100 mg/kg per day.

A subject to be treated for a disorder can be identified by standard diagnosing techniques for the disorder. Optionally, the subject can be examined for mutation, expression level, or activity level of one or more of DHODH, CKB, SLC6a8, miR-483-5p, and miR-551a mentioned above by methods known in the art or described above before treatment. If the subject has a particular mutation in the gene, or if the gene expression or activity level is, for example, greater (in the case for CKB or SLC6a8) in a sample from the subject than that in a sample from a normal person, the subject is a candidate for treatment of this invention.

To confirm the inhibition or treatment, one can evaluate and/or verify the inhibition of cancer cell survival, hypoxic survival, metastatic survival, or metastatic colonization using technologies known in the art before and/or after the administering step. Exemplary technologies include CT-scans or PET-scans of organs of the body.

The DHODH inhibitor or the pharmaceutically acceptable salt thereof and/or β-GPA or the pharmaceutically acceptable salt thereof can be administered to the subject intratumorally, intravenously, subcutaneously, intraosseously, orally, transdermally, in sustained release, in controlled release, in delayed release, as a suppository, or sublingually.

A therapeutic agent can be administered in vivo or ex vivo, alone or co-administered in conjunction with other drugs or therapy, i.e., a cocktail therapy. As used herein, the term “co-administration” or “co-administered” refers to the administration of at least two agent(s) or therapies to a subject. For example, in the treatment of tumors, particularly malignant tumors, the agents can be used alone or in combination with, e.g., chemotherapeutic, radiotherapeutic, apoptopic, anti-angiogenic agents and/or immunotoxins or coaguligands. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In some embodiments, the DHODH inhibitor or the pharmaceutically acceptable salt thereof is administered to the subject before (e.g., at least one day before, at least one week before, at least one month before), after (e.g., at least one day after, at least one week after, at least one month after), or concurrently with the β-GPA or the pharmaceutically acceptable salt thereof.

In some embodiments, this disclosure additionally provides a method comprising suppressing metastatic colonization of lung cancer in the liver of a subject in need thereof.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

In some embodiments, a dosage of the DHODH inhibitor or β-GPA can be one of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

β-GPA has the structure:

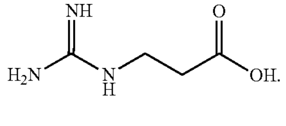

β-GPA is zwitterionic and highly soluble in water (>50 mg/mL), but has low solubility in organic solvents. β-GPA possesses a basic guanidino group and is thus capable of forming acid addition salts.

This disclosure further provides a method for treating colorectal cancer, gastric cancer, esophageal cancer, or pancreatic cancer in a subject in need thereof. In some embodiments, the cancer is cholangial cancer.

In some embodiments, the cancer expresses creatine kinase brain-type (CKB) (e.g., the cancer cells express CKB). In some embodiments, the cancer has been determined to express CKB based on histological examination of a tissue sample from the subject. In some embodiments, the subject has been identified as likely to respond to treatment with a DHODH inhibitor and β-GPA, or a pharmaceutically acceptable salt thereof (e.g., based on histological examination of a tissue sample from the subject to determine the level of CKB expression).

In some embodiments, the cancer expresses SLC6a8 (e.g., the cancer cells express SLC6a8). In some embodiments, the cancer has been determined to express SLC6a8 based on histological examination of a tissue sample from the subject. In some embodiments, the subject has been identified as likely to respond to treatment with a DHODH inhibitor and β-GPA, or a pharmaceutically acceptable salt thereof (e.g., based on histological examination of a tissue sample from the subject to determine the level of SLC6a8 expression) In some embodiments, the method further comprises administering to the subject one or more additional therapeutic agents, such as antitumor/anticancer agents, including chemotherapeutic agents and immunotherapeutic agents.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, methyldopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, xeloda, gemcitabine, KRAS mutation covalent inhibitors and goserelin; and pharmaceutically acceptable salts, acids or derivatives of any of the above. Additional examples include irinotecan, oxaliplatinum, and other standard colon cancer regimens.

An "immunotherapeutic agent" is a biological agent useful in the treatment of cancer. Examples of immunotherapeutic agents include atezolizumab, avelumab, blinatumomab, daratumumab, cemiplimab, durvalumab, elotuzumab, laherparepvec, ipilimumab, nivolumab, obinutuzumab, ofatumumab, pembrolizumab, cetuximab, and talimogene.

B. COMPOSITIONS AND KITS

In some embodiments, the DHODH inhibitor or the pharmaceutically acceptable salt thereof and the β-GPA or the pharmaceutically acceptable salt thereof are provided in a single composition. Alternatively, the DHODH inhibitor or the pharmaceutically acceptable salt thereof and the β-GPA or the pharmaceutically acceptable salt thereof can be provided in separate compositions.

Pharmaceutical compositions for use in accordance with the present methods may be formulated in a conventional manner using one or more physiologically acceptable carriers or excipients. Thus, the DHODH inhibitor and/or β-GPA, or their analogs/variants, described herein and their physiologically acceptable salts and solvates may be formulated for administration by, for example, injection, inhalation or insufflation (either through the mouth or the nose) or oral, buccal, parenteral or rectal administration. In one embodiment, the agent is administered locally, e.g., at the site where the target cells are present, such as by the use of a patch.

Pharmaceutical compositions can be formulated for a variety of loads of administration, including systemic and topical or localized administration. Techniques and formulations generally may be found in Remmington's Pharmaceutical Sciences, Meade Publishing Co., Easton, PA. For systemic administration, injection is preferred, including intramuscular, intravenous, intraperitoneal, and subcutaneous. For injection, the agents can be formulated in liquid solutions, preferably in physiologically compatible buffers such as Hank's solution or Ringer's solution. In addition, the agents may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

Pharmaceutical compositions that may oxidize and lose biological activity, especially in a liquid or semisolid form, may be prepared in a nitrogen atmosphere or sealed in a type of capsule and/or foil package that excludes oxygen (e.g., Capsugel™).

For administration by inhalation, the agents may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the agent and a suitable powder base such as lactose or starch.

Pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The agents may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The agents may also be formulated in rectal compositions such as suppositories or retention enemas, e.g., containing conventional suppository bases such as cocoa butter or other glycerides.

In addition to the formulations described previously, pharmaceutical compositions may also be formulated as a depot preparation. Such long acting formulations may be administered by implantation (for example, subcutaneously or intramuscularly) or by intramuscular injection. Thus, for example, the agents may be formulated with suitable polymeric or hydrophobic materials (for example, as an emulsion in an acceptable oil) or ion exchange resins, or as sparingly soluble derivatives, for example, as a sparingly soluble salt. Controlled release formula also includes patches, e.g., transdermal patches. Patches may be used with a sonic applicator that deploys ultrasound in a unique combination of waveforms to introduce drug molecules through the skin that normally could not be effectively delivered transdermally.

Pharmaceutical compositions (including cosmetic preparations) may comprise from about 0.00001 to 100%, such as from 0.001 to 10% or from 0.1% to 5% by weight of one or more agents described herein.

A pharmaceutical composition described herein can also be incorporated into a topical formulation containing a topical earner that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols, and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions, and gels. Pharmaceutical compositions may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Exemplary water-soluble ointment bases are prepared from polyethylene glycols (PEGs) of varying molecular weight; again, reference may be had to Remington's, supra, for further information.

Pharmaceutical compositions may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with hydrophilic petrolatum such as that which may be obtained under the trademark Aquaphor™ from Beiersdorf, Inc. (Norwalk, Conn.).

Pharmaceutical compositions may be incorporated into creams, which generally are viscous liquid or semisolid emulsions, either oil-in-water or water-in-oil. Cream bases are water-washable and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Pharmaceutical compositions may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives, and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprylic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Pharmaceutical compositions may be incorporated into gel formulations, which generally are semisolid systems consisting of either suspension made up of small inorganic particles (two-phase systems) or large organic molecules distributed substantially uniformly throughout a carrier liquid (single-phase gels). Single-phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose, and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients, and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation. A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{1O}$ MSO) and tetradecylmethyl sulfoxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkane diols; miscellaneous solvents such as dimethylformamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol™) and diethylene glycol monoethyl ether oleate (available commercially as Softcutol™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate). In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation. Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition.

In some embodiments, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

A composition described herein can be provided in a kit. In one embodiment, the kit includes (a) a container that contains the composition, and optionally (b) informational material. The informational material can be descriptive, instructional, marketing or other material that relates to the methods described herein and/or the use of the agents for therapeutic benefit. In an embodiment, the kit includes also includes an additional therapeutic agent. For example, the kit includes a first container that contains the composition and a second container for the additional therapeutic agent.

The informational material of the kits is not limited in its form. In one embodiment, the informational material can include information about production of the composition, concentration, date of expiration, batch or production site information, and so forth. In one embodiment, the informational material relates to methods of administering the composition, e.g., in a suitable dose, dosage form, or mode of administration (e.g., a dose, dosage form, or mode of administration described herein), to treat a subject in need thereof. In one embodiment, the instructions provide a dosing regimen, dosing schedule, and/or route of administration of the composition or the additional therapeutic agent. The information can be provided in a variety of formats, including printed text, computer-readable material, video recording, or audio recording, or information that contains a link or address to substantive material.

In addition to the composition, the kit can include other ingredients, such as a solvent or buffer, a stabilizer, or a preservative. The composition can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent and acidulant. The acidulant and solvent, e.g., an aprotic solvent, sterile water, or a buffer, can optionally be provided in the kit.

The kit can include one or more containers for the composition or compositions containing a DHODH inhibitor and/or β-GPA. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the DHODH inhibitor and β-GPA in a desired ratio. For example, the kit includes a plurality of syringes, ampules, foil packets, blister packs, or medical devices, e.g., each containing a single combination unit dose. The containers of the kits can be airtight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

C. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model.

"Treating" or "treatment" as used herein refers to administration of a compound or agent to a subject who has a disorder with the purpose to cure, alleviate, relieve, remedy, delay the onset of, prevent, or ameliorate the disorder, the symptom of a disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a non-human animal.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

As used herein, the term "modulate" is meant to refer to any change in biological state, i.e., increasing, decreasing, and the like.

The terms "increased," "increase" or "enhance" or "activate" are all used herein to generally mean an increase by a statically significant amount; for the avoidance of any doubt, the terms "increased," "increase" or "enhance" or "activate" means an increase of at least 10% as compared to a reference level, for example, an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "effective amount," "effective dose," or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

Doses are often expressed in relation to bodyweight. Thus, a dose which is expressed as [g, mg, or other unit]/kg (or g, mg etc.) usually refers to [g, mg, or other unit] "per kg (or g, mg etc.) bodyweight," even if the term "bodyweight" is not explicitly mentioned.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent," which is a biologically, physiologically, or pharmacologically active substance (or substances) that acts locally or systemically in a subject.

The terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) Blood 117:2423.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The terms "inhibit" and "antagonize," as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down-regulate a protein, a gene, and an mRNA stability, expression, function and activity, e.g., antagonists.

"Parenteral" administration of a composition includes, e.g., subcutaneous (s.c.), intravenous (i.v.), intramuscular (i.m.), or intrasternal injection, or infusion techniques.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism.

Multiple techniques of administering a compound exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

The term "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

D. EXAMPLES

Example 1

This example describes the materials and methods used in EXAMPLES 2-8 below.

Cell Culture

SW480, LS174T, and CT26 cell lines were obtained from ATCC. HEK-293LTV cells were obtained from Cell Biolabs. LS174T, HEK-293LTV, and CT26 cells were grown in Dulbecco's Modified Eagle Medium (Gibco) supplemented with 10% v/v fetal bovine serum (Corning), L-glutamine (2 mM; Gibco), penicillin-streptomycin (100 U/ml; Gibco), Amphotericin (1 μg/ml; Lonza), and sodium pyruvate (1 mM; Gibco). SW480 cells were grown in McCoy's 5A modified media with L-glutamine (Corning) supplemented with 10% v/v fetal bovine serum, penicillin-streptomycin (100 U/ml), Amphotericin (1 μg/ml), and sodium pyruvate (1 mM). All cells were grown at 37° C. under 5% $CO_2$ and passaged when the monolayer reached 80% confluency.

In Vitro Cell Growth Assays

CT26 cells that had been stably transduced with PCK1-targeting shRNA hairpins or control hairpins were grown in vitro for 3 days and counted on day 3 using the Sceptor 2.0 automated Cell counter (Millipore).

In Vitro Hypoxia Cell Growth Assays

Lvm3b cells or LS174T cells were grown under normoxia for 24 hours followed by incubation for 5 days under 0.5% oxygen and then counted using the Sceptor 2.0 automated Cell Counter (Millipore).

3-Mercaptopicolinic Acid In Vitro Growth Assay

LS174T cells were seeded in 6-well plates. On day 1, the media was replaced with either control media or media supplemented with 1 mM 3 MPA. On day 2, all the media was replaced with control media. The experiment was terminated on day 5.

A 24-hour exposure to 1 mM 3 MPA in media does not alter LS174T cell growth in vitro. $2\times10^4$ LS174T cells were seeded in triplicate. On day 1, the media was replaced with either control media or media supplemented with 1 mM 3 MPA. On day 2, all the media was replaced with control media. The experiment was terminated on day 5.

Stable Cell Lines

Lentiviral particles were created using the ViraSafe lentiviral packaging system (Cell Biolabs). ShRNA oligo sequences were based upon the Sigma-Aldrich MISSION shRNA library and were obtained from Integrated DNA technologies. The following shRNAs were used in this study: PCK1 sh3 (TRCN0000196706), PCK1 sh4 (TRCN0000199286), PCK1 sh5 (TRCN0000199573), shControl (SHC002), mouse PCK1 sh64 (TRCN0000025064), mouse PCK1 sh66 (TRCN0000025066), DHODH sh2 (TRCN0000221421), and DHODH sh3 (TRCN0000221422). Forward and reverse complement oligos were annealed, cloned into pLKO, and transformed into XL10-Gold *E. coli* (200314, Agilent). For PCK1 overexpression, PCK1 cDNA (plasmid ID HsCD00045535) was obtained from the PlasmID Repository at Harvard Medical School and cloned into pBabe-puromycin. For tetracycline-inducible experiments, the seed sequences of shRNA control (SHC002) or PCK1 sh4 (TRCN0000199286) were cloned into pLKO-Tet-On (Wiederschain et al., 2009). All plasmids were isolated using the plasmid plus midi kit (Qiagen). Transduction and transfection were performed as described previously (F. Yu, et al. *Cancer Lett* 368, 135-143 (2015)).

Animals Studies

All animal work was conducted in accordance with a protocol approved by the Institutional Animal Care and Use Committee (IACUC) at The Rockefeller University and Memorial Sloan Kettering Cancer Center. Either NOD.Cg-Prkdc$^{scid}$ Il2rg$^{tm1Wjl}$/SzJ (Nod-Scid-Gamma; NSG) aged 6-10 weeks or Foxn1$^{nu}$(Nu/J; athymic nude) aged 6-10 weeks were used for all mouse experiments. For functional studies of PCK1, colorectal cancer cells (SW480 or LS174T) that had been stably transduced with a luciferase reporter (Ponomarev et al., 2004) were subjected to portal circulation injection in NSG mice; after two minutes, a splenectomy was performed. For functional and pharmacology studies of DHODH, colorectal cancer cells (Lvm3b) that had been stably transduced with a luciferase reporter were subjected to portal circulation injection in athymic nude mice; after two minutes, a splenectomy was performed. Mice were imaged weekly; experiments were terminated when the luciferase signal had saturated or the mice were too ill, whichever occurred first.

Administration of 3-Mercaptopicolinic Acid and Leflunomide In Vivo

Chow was removed from cages four hours prior to injection of LS174T cells. Gavage with either 3-MPA (200 mg/kg in aqueous solution) or placebo was performed one hour prior to the injection of LS174T cells. 1×106 LS174T cells were injected into the portal systemic circulation as described in the Animals section above. Chow was returned to cages after injection. On day 1, chow was removed from cages; 3-MPA or placebo was administered via gavage four hours post-chow removal. Chow was returned to cages four hours after drug administration. Mice were imaged bi-weekly. Leflunomide (Tocris Cat #2228) 7.5 mg/kg mouse body weight were intraperitoneally injected every day. An equivalent volume of DMSO was intraperitoneally injected every day to the control cohort.

Histology

Patient colorectal tumors were prepared and stained with hematoxylin and eosin (H&E) per standard clinical procedures following surgical resection of the tumor specimen. Subcutaneous and liver xenograft samples were removed from the mice at the time of sacrifice and fixed in 4% paraformaldehyde solution for 48 hours at 4°. The xenografts samples were subsequently rinsed in PBS twice followed by one-hour incubations in 50% ethanol, then 70% ethanol. The xenografts samples were stained with maintained in 70% ethanol at 4°. The fixed xenografts samples were embedded in paraffin, sectioned, and stained with H&E (Histoserv).

Quantitative RT-PCR qRT-PCR was performed to confirm expression of PCK1. Total RNA was extracted (37500, Norgen) from CRC PDXs, SW480, LS174T, or CT26 cells that had been stably transduced with PCK1-targeting shRNA hairpins, control hairpins, pBabe-PCK1, or pBabe-control. cDNA was generated using Superscript III first strand cDNA synthesis kit (18080051, Invitrogen) per manufacturer's protocol. For quantification of cDNA, Fast SYBR Green Master Mix (4385612, Applied Biosystems) was used for sample analysis. Gene expression was normalized to HPRT expression. The following sequences were used as primers for CRC PDXs, SW480, and LS174T cells: PCK1-F, AAGGTGTTCCCATTGAAGG (SEQ ID NO: 1); PCK1-R, GAAGTTGTAGCCAAAGAAGG (SEQ ID NO: 2); HPRT-F, GACCAGTCAACAGGGGACAT (SEQ ID NO: 3); HPRT-R, CCTGACCAAGGAAAGCAAAG (SEQ ID NO: 4). The following sequences were used as primers for CT26 cells: PCK1-F, CTGCATAACGGTCTGGACTTC (SEQ ID NO: 5); PCK1-R, CAGCAACTGCCCGTACTCC (SEQ ID NO: 6); b-actin-F, GGCTGTATTCCCCTCCATCG (SEQ ID NO: 7); b-actin-R, CCAGTTGGTAACAATGCCATGT (SEQ ID NO: 8). The following primers were used for Lvm3b cells: DHODH-F, CCACGGGAGATGAGCGTTTC (SEQ ID NO: 9); DHODH-R, CAGGGAGGT-GAAGCGAACA (SEQ ID NO: 10)

Clinical Analysis

GEO data sets GSE41258, GSE 507060, GSE14297, and GSE6988 were used to evaluate for expression of PCK1 as described previously (F. Yu, et al. *Cancer Lett* 368, 135-143 (2015); S. K. Kim, et al. *Mol Oncol* 8, 1653-1666 (2014)).

Patient-Derived Colorectal Cancer Xenografts

Within 2 hours of surgical resection, colorectal cancer tumor tissue that was not needed for diagnosis was implanted subcutaneously into NSG mice at the MSKCC Antitumor Assessment Core facility. When the tumor reached the pre-determined end-point of 1,000 $mm^3$, the tumor was excised and transferred to the Rockefeller University. Xenograft tumor pieces of 20-30 $mm^3$ were reimplanted. When the subcutaneous tumor reached 1,000 $mm^3$, the tumor was excised. Part of the tumor was cryogenically frozen in FBS:DMSO (90:10) for future use. The rest of the tumor was chopped finely with a scalpel and placed in a 50 ml conical tube with a solution of Dulbecco's Modified Eagle Medium (Gibco) supplemented with 10% v/v fetal bovine serum (Corning), L-glutamine (2 mM; Gibco), penicillin-streptomycin (100 U/ml; Gibco), Amphotericin (1 μg/ml; Lonza), sodium pyruvate (1 mM; Gibco) and Collagenase, Type IV (200 U/ml; Worthington) and placed in a 37° C. shaker at 220 rpm for 30 minutes.

After centrifugation and removal of the supernatant, the sample was subjected to ACK lysis buffer (Lonza) for 3 minutes at room temperature to remove red blood cells. After centrifugation and removal of ACK lysis buffer, the sample was subjected to a density gradient with Optiprep (1114542, Axis-Shield) to remove dead cells. The sample was washed in media and subjected to a 100 μm cell strainer and followed by a 70 μm cell strainer. Mouse cells were removed from the single-cell suspension via magnetic-associated cell sorting using the Mouse Cell Depletion Kit ((130-104-694, Miltenyi), resulting in a single cell suspension of predominantly colorectal cancer cells of human origin. One million PDX colorectal cancer cells were injected into the portal circulation of NSG mice via the spleen. Two minutes after injection, the spleen was removed using electrocautery. When the mouse was deemed ill by increased abdominal girth, slow movement, and pale footpads, it was euthanized and the tumors were removed and sectioned in a manner similar to the subcutaneous implants. For a subset of mice (CLR4, CLR27, CLR28, CLR32) the CRC liver metastatic tumor cells were injected into the spleens of another set of NSG mice in order to obtain metastatic derivatives with enhanced ability to colonize the liver.

Flow Cytometric Cell Sorting and RNA Sequencing

To ensure minimal contamination from mouse stromal or blood cells during RNA sequencing, flow cytometric cell sorting of the PDX cell suspension was performed after it had been processed through the magnetic-based mouse cell depletion kit (130-104-694, Miltenyi). Single cells that bound an APC-conjugated anti-human CD326 antibody (324208, BioLegend) and did not bind to a FITC-conjugated anti-mouse H-2Kd antibody (116606, BioLegend) were positively selected and considered to be PDX colorectal cancer cells. RNA was isolated from these double-sorted CRC PDX cells (37500, Norgen), ribosomal RNA was removed (MRZH11124, Illumina), and the samples were prepared for RNA-sequencing using script-seq V2 (SSV21124, Illumina). RNA sequencing was performed by the RU Genomics Resource Center on an Illumina HiSeq 2000 with 50 basepair single read sequencing. The sequencing data was cleaned of low-quality base pairs and trimmed of linker sequences using CUTADAPT (v1.2) and aligned to the reference transcriptome (Hg19) using TopHat (v2). Cufflinks (v2) was used to estimate transcript abundances. Upon merging assemblies (Cuffmerge), comparison of samples was made using Cuffdiff (v2) to determine genes that were differentially expressed between parental and liver-metastatic derivative xenografts. Fisher's method was used to determine genes that were differentially expressed across all analyzed gene sets.

Gene Expression Profile Clustering

Correlation matrix of gene expression profiles from RNA sequencing was generated using Spearman's correlation coefficient. Clustering was performed in R using Euclidean distance and complete agglomeration method.

Gene Set Enrichment Analysis (GSEA)

Each isogenic tumor pair (parental and liver-metastatic derivative) was evaluated for changes in the Hallmark gene sets using GSEA (v2.2.1, Broad Institute). Additionally, a composite gene set using Fisher's method as described in the section above was analyzed using GSEA.

Metabolite Extraction

Metabolite extraction and subsequent Liquid-Chromatography coupled to High-Resolution Mass Spectrometry (LC-HRMS) for polar metabolites of cells were carried out using a Q Exactive Plus. Shctrl or shPCK1 LS174T were plated at 300,000 cells/well in triplicate with RPMI1640+dialyzed FBS+6 mM glucose and remained in 0.5% $O_2$ or normoxia for 24 hr. For PDX metabolite profiling, 100 mg of frozen PDXs were used. For all metabolite profiling, cells were washed with ice-cold 0.9% NaCl and harvested in ice-cold 80:20 LC-MS methanol:water (v/v). Samples were vortexed vigorously and centrifuged at 20,000 g at maximum speed at 4° C. for 10 min. The supernatant was transferred to new tubes. Samples were then dried to completion using a nitrogen dryer. All samples were reconstituted in 30 μl 2:1:1 LC-MS water:methanol:acetonitrile. The injection volume for polar metabolite analysis was 5 μl.

Liquid Chromatography

A ZIC-pHILIC 150×2.1 mm (5 μm particle size) column (EMD Millipore) was employed on a Vanquish Horizon UHPLC system for compound separation at 40° C. The autosampler tray was held at 4° C. Mobile phase A is water with 20 mM Ammonium Carbonate, 0.1% Ammonium Hydroxide, pH 9.3, and mobile phase B is 100% Acetonitrile. The gradient is linear as follows: 0 min, 90% B; 22 min, 40% B; 24 min, 40% B; 24.1 min, 90% B; 30 min, 90% B. The flow rate was 0.15 ml/min. All solvents are LC-MS grade and purchased from Fisher Scientific.

Mass Spectrometry

The Q Exactive Plus MS (Thermo Scientific) is equipped with a heated electrospray ionization probe (HESI) and the relevant parameters are as listed: heated capillary, 250° C.; HESI probe, 350° C.; sheath gas, 40; auxiliary gas, 15; sweep gas, 0; spray voltage, 3.0 kV. A full scan range from 55 to 825 (m/z) was used. The resolution was set at 70,000. The maximum injection time was 80 ms. Automated gain control (AGC) was targeted at $1\times10^6$ ions. Maximum injection time was 20 msec.

Peak Extraction and Data Analysis

Raw data collected from LC-Q Exactive Plus MS was processed on Skyline (skyline.ms/project/home/software/Skyline/begin.view?) using a 5 ppm mass tolerance and an input file of m/z and detected retention time of metabolites from an in-house library of chemical standards. The output file including detected m/z and relative intensities in different samples was obtained after data processing. Quantitation and statistics were calculated using Microsoft Excel, GraphPad Prism 8.1, and Rstudio 1.0.143.

Statistics

Kaplan-Meier analysis was used to evaluate patient survival based upon PDX parameters. Sample size in mouse experiments was chosen based on the biological variability observed with a given genotype. Non-parametric tests were used when normality could not be assumed. Mann Whitney test and t-test were used when comparing independent shRNAs to shControl. One-tailed tests were used when a difference was predicted to be in one direction; otherwise, a two-tailed test was used. A P value less than or equal to 0.05 was considered significant. (*: P<0.05, :p<0.01, *: p<0.001, and ****: p<0.0001) Error bars represent SEM unless otherwise indicated.

Study Approval

Approval for the study was obtained through the MSKCC Institutional Review Board/Privacy Board (protocol 10-018A), the MSKCC Institutional Animal Care and Use Committee (protocol 04-03-009), The Rockefeller University Institutional Review Board (protocol STA-0681), and The Rockefeller University Institutional Animal Care and Use Committee (protocol 15783-H). Written consent was obtained from all human participants who provided samples for patient-derived xenografts.

Example 2

Liver Growth and Engraftment Rates of CRC PDXs Predict Patient Outcomes

In order to establish a PDX model of CRC liver metastatic colonization, a small sample of colorectal cancer tissue, taken either from a primary or metastatic site, was dissociated and injected subcutaneously into the flanks of NOD.Cg-Prkdc$^{scid}$ Il2rg$^{tm1Wjl}$/SzJ (Nod-Scid-Gamma; NSG) mice within two hours of surgical resection at MSKCC. Thirty-one subjects provided forty tumor samples; 48.3% of the subjects' samples engrafted. The majority of subjects in this study were classified as Stage IV colorectal cancer according to the American Joint Committee on Cancer (AJCC). However, AJCC stage was not associated with increased xenograft engraftment (p=0.35; $\chi^2$ test). The engraftment rates for tumor tissues that originated from the colon and the liver were similar (40% vs 37.5%). Most subjects had undergone chemotherapy prior to surgical resection of metastases (67.7%). When categorizing tumors by commonly tested clinical mutations (KRAS, high microsatellite instability (MSI-H), NRAS, BRAF, PIK3CA, and none), MSI-H tumors exhibited the highest engraftment rates (83.3%), while tumors lacking these commonly tested for clinical mutations exhibited the lowest engraftment rates (18.2%).

It was found that subcutaneous tumor engraftment was associated with worse patient survival (p=0.045). The time from subcutaneous tumor implantation to tumor harvest ranged from 35 to 88 days. Among those CRC tumors that did grow subcutaneously, the time to reach the pre-determined tumor size (1,000 $mm^3$) was not significantly associated with patient survival (p=0.27). When the estimated subcutaneous tumor volume reached 1,000 $mm^3$, the mice were euthanized, and the tumors were removed. For each sample, a portion of the xenografted tumor was set aside for cryopreservation, and the rest of the tumor was dissociated into a single cell suspension for portal circulation injection via the spleen.

Portal circulation injection has been demonstrated to be a reliable means of establishing liver growth via a hematogenous spread of CRC cells, simulating the entry of cells into the portal circulation which is typical of clinical CRC progression. After injection of cells, the mice were observed until they were deemed ill by increased abdominal girth, slow movement, and pale footpads, at which point euthanization and tumor extractions were performed. Successful liver metastatic colonization was achieved upon injection of 15/17 patient samples. The time to mouse sacrifice for the CRC patient-derived liver xenografts ranged from 51 to 407 days and did not correlate with subcutaneous tumor growth rates ($R^2$=0.046, p=0.50). The mCRC liver PDXs fell into two biologically distinct groups based on their growth rates: one set grew quickly, requiring mouse euthanasia within three months of implantation; the other set grew more slowly, requiring animal sacrifice after six months, or even one-year, post-engraftment. Importantly, these two groups of PDXs exhibited similar growth rates when implanted subcutaneously (p=0.09). This suggests distinct selective pressures for PDX growth existing in the liver relative to the subcutaneous microenvironment. It was found that the liver colonization model mimicked clinical outcomes, as patients whose xenografts rapidly colonized mouse livers fared poorly relative to patients whose xenografts colonized the liver slowly or not at all (p=0.031). Taken together, these results establish that the CRC liver metastasis PDX modeling described above is prognostic of clinical outcomes.

A key objection to cell line xenografts is that the histology of animal tumors is often not representative of clinical sample histology. Contrary to this, it was observed that both subcutaneous and liver engrafted tumors re-capitulated the architecture of the primary tumor from which they were derived. CLR4 was established from a poorly differentiated liver metastatic colon adenocarcinoma; it remained poorly differentiated in both the subcutaneous and liver xenografts. Similarly, CLR32 and CLR28 were derived from moderate-to-well differentiated primary colon and peritoneal metastatic adenocarcinomas and retained their moderate-to-well differentiated histology when passaged subcutaneously and hepatically.

Example 3

Generation of In-Vivo Selected Highly Liver Metastatic PDXs

Liver-directed in vivo selection through iterative splenic injections of four distinct CRC PDXs was performed with varying mutational and metastatic backgrounds to obtain derivatives with increased capacity for liver colonization and growth (FIG. 1). Tumors were only passaged in vivo without the use of in vitro culture. When a mouse bearing a liver colonization graft had met its pre-determined endpoint, it was euthanized and the liver tumor was removed and dissociated into a single cell suspension in a similar manner to that of the subcutaneous tumors described above. Dissociated cells were subsequently injected into the spleen of another mouse to generate a second-generation liver metastatic derivative. This process was repeated multiple times to create a highly metastatic derivative for each of the four distinct CRC PDXs. The number of rounds of in vivo selection varied between tumor samples (range: 5-13) and in general, tended to represent the number of rounds required to plateau enhanced metastatic colonization capacity. In the last round of in vivo selection, a cohort of mice was subjected to portal circulation injection with either the parental CRC PDX cells or the liver-metastatic derivative CRC PDX cells in order to assess the relative liver colonization capacities among the liver-metastatic derivatives. In each of the four CRC PDX comparisons, the in vivo-selected CRC PDX liver metastatic derivatives colonized the mouse liver more efficiently than their parental counterparts (FIG. 1). The two extreme isogenic populations of each patient, the parental CRC PDX and its liver-metastatic derivative, were then subjected to transcriptomic and metabolite profiling as described below to identify candidate regulators of metastatic colonization.

Example 4

Candidate Metastasis Promoting Genes Identified Through Transcriptomic Profiling of Metastatic CRC PDXs Candidate mCRC liver colonization promoters were identified through mRNA sequencing and differential gene expression analyses from parental CRC PDXs (anatomical locations included subcutaneous graft, cecal graft, or first-generation liver graft) and last generation liver-metastatic CRC PDXs. Comparisons between liver metastatic derivatives and their parental counterparts allowed for isogenic comparisons. A phylogenetic tree using complete clustering and Euclidian distance function based upon the gene expression profiles demonstrated that isogenic pairs mostly clustered together with one exception.

Each of the four pairs of tumors individually and as a composite were interrogated using gene set enrichment analysis (GSEA) to identify cancer-related pathways and signatures that were significantly altered in liver metastatic derivatives compared to their isogenic parental xenografts (A. Subramanian, et al. *Proc Natl Acad Sci USA* 102, 15545-15550 (2005)). The hypoxia signature was found to be upregulated in all of the liver metastatic derivatives individually and in the composite, where it was the most significantly enriched gene signature (normalized enrichment score (NES)=2.12, q-value<0.001). Upregulation of hypoxia genes in the liver metastatic derivatives is consistent with previous reports demonstrating that hypoxia exerts selective pressure in the liver metastatic microenvironment (J. M. Loo, et al. *Cell* 160, 393-406 (2015); A. Nguyen, et al. *J Clin Invest* 126, 681-694 (2016)).

With each CRC PDX pair, upregulated genes were identified in each liver-metastatic derivative compared to its parental counterpart through a generalized linear model. The number of upregulated genes ($p<0.05$) in the liver-metastatic derivatives ranged from 200 (CLR28) to 345 (CLR27) out of a possible list of more than 12,000 genes. Fisher's combined probability test was used to construct a list of candidate liver colonization promoting genes that were statistically significantly upregulated across the four pairs of CRC PDXs with an effect size of greater than 1.5 $\log_2$ fold change (log FC). Using this approach, 24 highly up-regulated genes were identified in the liver metastatic derivatives, with the ten most highly up-regulated genes annotated on the volcano plot. Interestingly, two of the top ten up-regulated genes (IFITM1, and CKB) have been previously implicated as promoters of colorectal cancer metastasis. The most common 'druggable' targets for cancer therapeutics are enzymes and cell-surface receptors. In the list of candidate genes, three were enzymes (ACSL6, CKB, and PCK1) and one was a cell-surface receptor (CDHR1).

One of the genes on this list, creatine kinase-brain (CKB), was identified by us in a prior study using established colorectal cancer cell lines and shown to regulate tumoral phosphocreatine and ATP levels in the hypoxic microenvironment of the liver (J. M. Loo, et al. *Cell* 160, 393-406 (2015)). Of the remaining three enzymes on the list, the analysis was focused on evaluating the role of phosphoenolpyruvate carboxykinase 1 (PCK1), given the availability of a pharmacological inhibitor and its heightened expression in normal liver, suggesting potential mimicry of hepatocytes by colorectal cancer cells during adaptation to the liver microenvironment.

Whether the 24-gene candidate CRC liver colonization signature was enriched in liver metastases from patients with colorectal cancer was investigated by querying a publicly available dataset in which transcriptomes of primary CRC tumors and liver metastases were profiled. Of the twenty-four genes, twenty-two were represented in this previously published dataset (M. Sheffer, et al. *Proc Natl Acad Sci USA* 106, 7131-7136 (2009)). The patient data was binned based upon differential gene expression in the primary CRC tumors versus the CRC liver metastatic tumors. The up-regulated genes were significantly enriched ($p=0.007$) in the bin with the most upregulated genes in CRC liver metastases, supporting the clinical relevance of the in vivo-selected CRC PDX liver colonization mouse model. In further support of the clinical relevance of the findings presented herein, it was found that the gene expression up-regulation in the metastatic CRC system significantly correlated (rho=0.39, $p=0.047$) with the gene expression up-regulation in human liver CRC metastases relative to CRC primary tumors. Interestingly, PCK1 was highly up-regulated in human CRC liver metastases relative to primary tumors. QPCR quantification confirmed PCK1 gene expression up-regulation in liver metastatic derivatives relative to isogenic parental counterparts. Other publicly available colorectal cancer gene expression datasets were analyzed and consistently observed PCK1 to be significantly upregulated ($p=0.01$, Student t-test) in CRC liver metastases relative to primary tumors. Additionally, PCK1 was upregulated ($p=0.01$; FIG. 3F, $p<0.0001$) in CRC liver metastases in datasets containing only paired CRC primary tumors and CRC liver metastases obtained from the same patients.

Example 5

PCK1 Promotes Colorectal Cancer Liver Metastatic Colonization

Functional in vivo studies were performed using human colorectal cancer cell lines in which PCK1 expression was modulated through stable gene knockdown or overexpression. Depletion of PCK1 in SW480 cells by two independent shRNAs significantly impaired ($p<0.0001$ in both comparison) colorectal cancer liver metastatic colonization of cells introduced into the portal circulation of NSG mice. PCK1 depletion in another colorectal cell line (LS174T) also significantly decreased ($p<0.0001$) liver metastatic colonization. Conversely, PCK1 over-expression in SW480 cells significantly increased ($p=0.003$) liver metastatic colonization. In contrast, PCK1 depletion did not impact subcutaneous tumor growth in the SW480 or LS174T cell lines.

To assess whether PCK1 modulation regulated cancer progression in a fully immunocompetent model as well, PCK1 in the murine colorectal cancer cell line CT26 was depleted. Consistent with the observations in human cancer lines, PCK1 depletion decreased murine colorectal cancer cell liver colonization in an immune-competent model ($p=0.039$ and $p=0.005$ for shCTRL vs. shPCK1064, shCTRL vs. shPCK1-66, respectively) and did not impair in vitro proliferation under basal cell culture conditions.

It is important to determine the cellular mechanism by which PCK1 impacts metastatic colonization; that is, whether PCK1 influences initial colorectal cancer cell liver colonization, apoptosis, or population growth. To identify whether initial liver colonization was the sole step in the metastatic cascade influenced by PCK1 or whether it could provide continued impact on colorectal cancer liver growth, SW480 cells were generated expressing an inducible PCK1 shRNA. Four days after portal-systemic injection of cancer cells, at which time CRC cells have extravasated into the liver and begun initial outgrowth, administration of doxycycline or a control diet was started. It was found that even after the initial liver colonization phase (days 0-4), PCK1 depletion continued to impair ($p=0.004$) colorectal cancer metastatic liver growth. Increased apoptosis was not observed using the caspase 3/7 reporter in both PCK1 depleted cell populations in vivo. Evaluation of the in vivo growth rate through natural log slope calculations demonstrated that in each PCK1 modulation experiment, either knockdown or overexpression, in which a luciferase reporter was used, the rate of growth after the first measured time point (day 4-7) did not equal the rate of growth of the controls. These results reveal that PCK1 promotes the rate of metastatic growth in vivo.

Example 6

Metabolic Profiling Reveals PCK1-Dependent Pyrimidine Nucleotide Biosynthesis in CRC Under Hypoxia Given inventors' identification of PCK1 as a metabolic regulator of CRC liver metastatic colonization as well as the enrichment of a hypoxic signature by GSEA in highly metastatic PDXs, it was speculated that PCK1 may promote metabolic adaptation that enables growth under hypoxia—a key feature of the hepatic microenvironment. Consistent with this, depletion of PCK1 in CRC cells significantly impaired hypoxic viability. Interestingly, depletion of PCK1 in CRC cells did not affect viability under normoxic conditions.

Figure 2A:
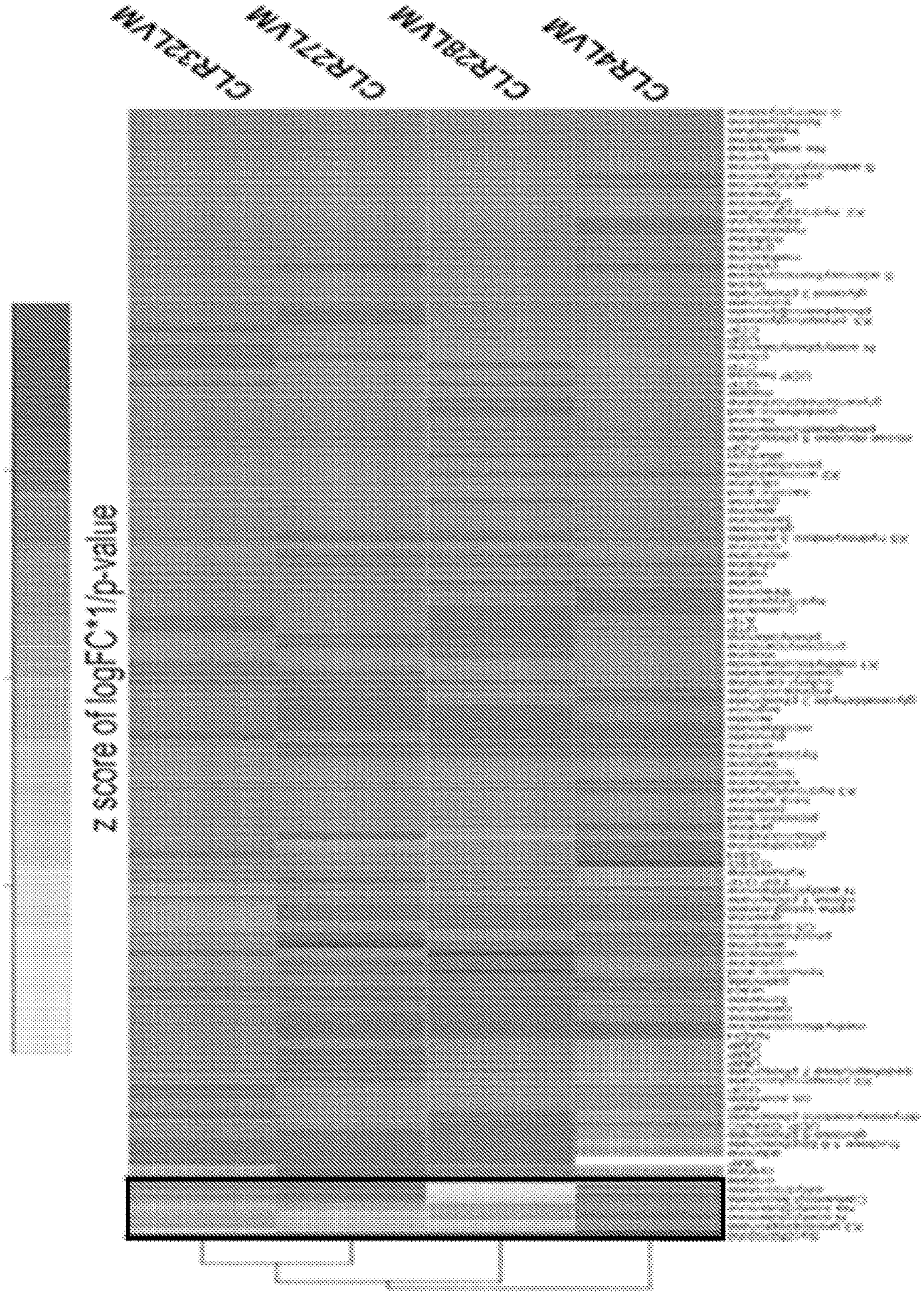
FIGS. 2A and 2B (collectively "FIG. 2") are a set of diagrams showing the unsupervised hierarchical clustering of 170 polar metabolites' profiling data.
Figure 2B:
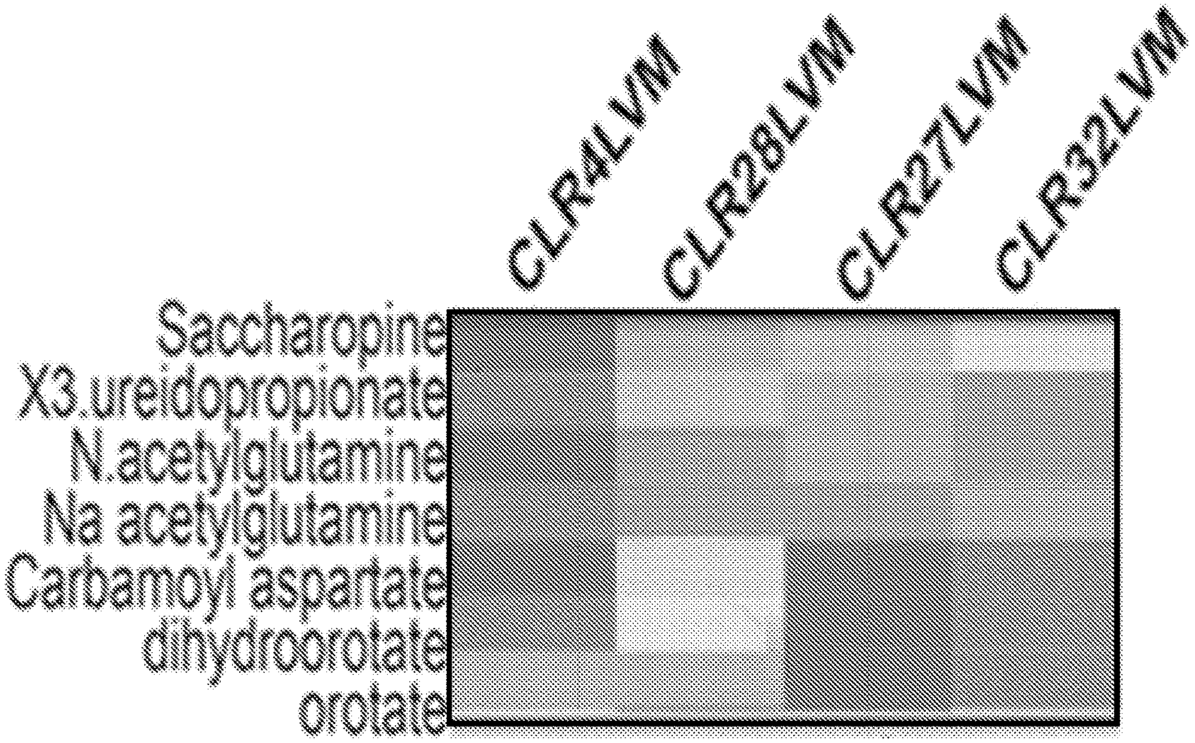

Hypoxia poses a metabolic challenge for cancer cell growth as metabolites needed for biosynthesis of macromolecules required for cell proliferation can become limiting. In vivo selected cancer cells can alter cellular metabolism in order to better respond to the metastatic microenvironment. To search for such adaptive metastatic metabolic alterations that associate with enhanced PCK1 expression, metabolomic profiling of the four highly/poorly metastatic CRC PDX pairs was performed. Unsupervised hierarchical clustering analysis was then performed on the differentially expressed metabolite profiles for each pair. Interestingly, the most salient observation was increased abundance in three out of four PDX pairs of multiple nucleoside base precursors and specific metabolites in the pyrimidine biosynthetic pathway (FIGS. 2A and 2B). These metabolites comprised orotate, dihydroorotate, and ureidopropionate. These findings revealed that metastatic colonization by human CRC cells selects for induction of multiple metabolites in the pyrimidine biosynthetic pathway.

It was thus hypothesized that enhanced levels of pyrimidine precursors were selected for in metastatic CRC cells to enable adaptation to hypoxia where precursors for pyrimidine biosynthesis, such as aspartate, are known to become depleted (K. Birsoy, et al. *Cell* 162, 540-551 (2015); L. B. Sullivan, et al. *Nat Cell Biol* 20, 782-788 (2018)). Without such an adaptation, cells would experience deficits in pyrimidine bases and consequently nucleotide pools, which would curb growth. Thus, it remained to be investigated how PCK1 upregulation contributes to the maintenance of nucleotide pools. Nucleotides contain nitrogenous bases covalently coupled to ribose and phosphate. PCK1 was previously shown to promote ribose generation by CRC cells under pathophysiological levels of glucose via the pentose phosphate pathway (E. D. Montal, R. Dewi, et al. *Mol Cell* 60, 571-583 (2015)). It was thus hypothesized that PCK1 depletion may reduce pyrimidine and purine nucleotide pools in CRC cells. To test this, metabolite profiling of control and PCK1 depleted CRC cells under hypoxia were performed. While metabolites related to glycolysis and the citric acid (TCA) cycle were significantly increased, the most salient finding was a significant depletion of nucleosides and nucleotides including uridine, guanine, UMP, CMP, CDP, IMP, GMP, and AMP. Consistent with the cell viability findings, these decreases in nucleoside and nucleotide levels were abrogated under normoxic conditions. These findings reveal that PCK1 expression is required for nucleotide pool maintenance in CRC cells in the context of hypoxia.

The above findings reveal that liver metastatic CRC cells enhance pyrimidine levels and that PCK1 drives pyrimidine nucleotide levels under hypoxia. These findings also suggest that hypoxia acts as a barrier to growth for metastatic CRC by limiting pyrimidine nucleoside levels. To directly test this, whether the growth defect of PCK1 depletion upon hypoxia could be rescued by the pyrimidine nucleoside uridine was determined. Indeed, supplementation of CRC cells with uridine rescued the hypoxic growth defect observed upon PCK1 depletion. The results reveal PCK1 induction to be a mechanism employed by CRC cells to enhance pyrimidine nucleotide levels under hypoxia to promote growth.

Example 7

Inhibition of PCK1 or DHODH Suppresses CRC Liver Metastatic Colonization

Due to the strong reduction in mCRC liver colonization observed upon PCK1 depletion, it was hypothesized that PCK1 inhibition may represent a potential therapeutic strategy for impairing CRC metastatic progression. In vivo proof-of-principle experiments were performed in two independent CRC cell lines with a PCK1-inhibitor, 3-mercaptopicolinic acid (3-MPA) (N. W. DiTullio, et al. *Biochem J* 138, 387-394 (1974)). CRC cells were treated in vitro for 24 hours at a dose that did not alter cell proliferation in vitro. The following day, mice were subjected to portal circulation injections with either control or 3-MPA-treated cells. Similar to PCK1 inhibition by shRNA, pre-treatment of cells with 3-MPA significantly reduced (p=0.01) mCRC liver colonization in vivo. Pre-treatment of LS174T cells with 3-MPA did not, however, alter subcutaneous tumor growth. Next, whether experimental therapeutic delivery of 3-MPA could suppress metastatic colonization was tested. Prior to portal-systemic injection of LS174T cells, oral gavage treatment of mice was started with either 200 mg/kg of 3-MPA in aqueous solution or control. On day one, the 3-MPA or control gavage was repeated. It was found that even such short-term treatment of 3-MPA decreased colorectal cancer liver colonization in this model. Taken together, these results indicate that PCK1 promotes colorectal cancer liver colonization and represents a potential target for which therapeutics could be developed as a means of reducing CRC for metastatic relapse.

Dihydroorotate Dehydrogenase (DHODH) is a key enzyme in the metabolic pathway that reduces dihydroorotate to orotate, which is ultimately converted to the pyrimidine nucleotides UTP and CTP. To further confirm that pyrimidine biosynthesis promotes CRC hypoxic growth, CRC growth upon DHODH inhibition was assessed. Leflunomide is an approved, well-tolerated, and high-affinity (Kd=12 nM) small-molecule inhibitor of DHODH used in the treatment of rheumatoid arthritis. Leflunomide treatment significantly impaired CRC growth in the context of hypoxia—an effect that was more significant under hypoxia than normoxia. These results confirm that metastatic CRC cell growth under hypoxia is sensitive to pyrimidine biosynthesis inhibition.

Figure 3A:
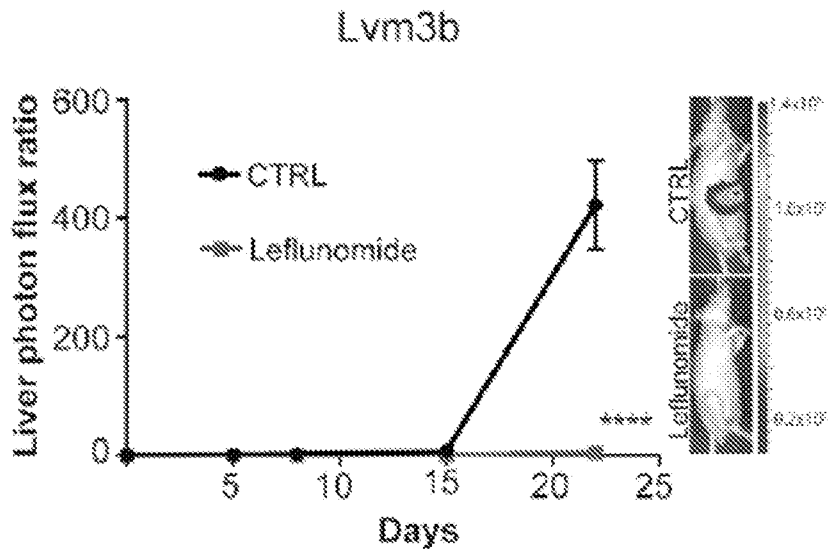
FIGS. 3A and 3B are a set of diagrams showing the effects of the DHODH inhibitor in inhibiting liver metastatic colonization.
Figure 3B:
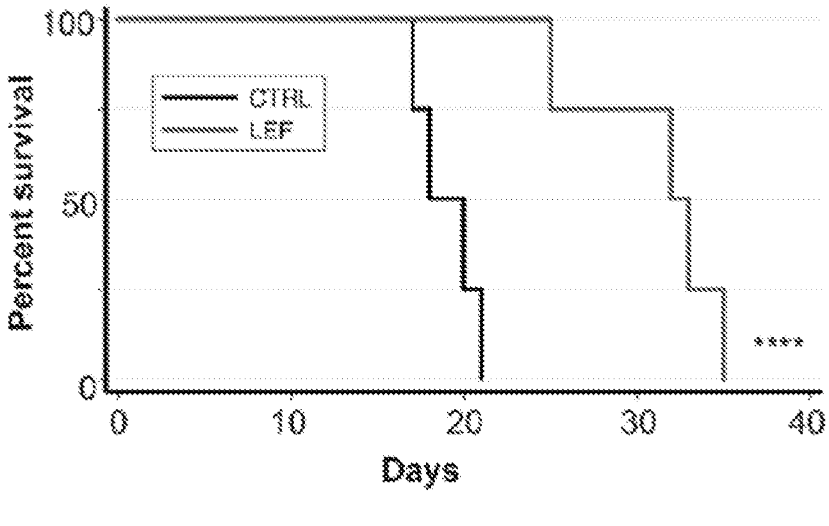

The results presented herein suggest that metastatic CRC liver metastatic colonization may be sensitive to inhibition of the pyrimidine biosynthetic pathway. To directly test this, highly metastatic LVM3b CRC cells of DHODH were depleted. DHODH depletion substantially reduced CRC liver metastatic colonization, indicating a critical role for DHODH activity and pyrimidine biosynthesis in CRC liver metastatic colonization. To determine if leflunomide can therapeutically inhibit CRC liver metastasis, animals were treated with a dose of this drug similar to that used for rheumatoid arthritis (7.5 mg/kg body weight). Treatment of animals injected with highly metastatic Lvm3b cells with leflunomide caused a ~90-fold reduction in CRC liver metastatic colonization (FIG. 3A). The leflunomide treated mice experienced significantly longer survival (p=0.006) than the control mice (FIG. 3B). Importantly, these cells are known to be highly resistant to 5-FU (K. Bracht, et al. Br J Cancer 103, 340-346 (2010)), the backbone chemotherapeutic used in CRC, indicating that inhibition of DHODH can exert therapeutic benefit despite cellular resistance to an anti-metabolite that targets the pyrimidine pathway. Leflunomide treatment only modestly impacted primary tumor growth by two distinct CRC populations, suggesting a preferential sensitivity of CRC cells to leflunomide-mediated DHODH inhibition during liver metastatic colonization.

To determine if the metastatic colonization defect caused by leflunomide treatment is caused by pyrimidine depletion, cell growth suppression was tested in the presence or absence of uridine—the downstream metabolic product of the pyrimidine biosynthetic pathway. It was found that the impaired growth upon hypoxia was rescued upon uridine supplementation. Importantly, leflunomide treatment impaired proliferation significantly more in the context of hypoxia than under normoxia. These observations show that highly metastatic cells exhibit enhanced dependence on pyrimidine biosynthesis and upregulation of metabolites in this pathway as a selective adaptive trait of highly metastatic CRC cells. Overall, the results identify DHODH as a therapeutic target in CRC progression and provide proof-of-concept for the use of leflunomide in therapeutic inhibition of CRC metastatic progression.

Example 8

Synergetic Effects of the DHODH Inhibitor and/3-GPA

To test whether a combination of DHODH inhibition and SLC6a8 inhibition can be therapeutically exploited in gastrointestinal cancer models, 1 million MC38 cells were subcutaneously injected into $C_{57}$BL/6 mice (n=4 per each cohort) (FIG. 4A). Intraperitoneal leflunomide injection was started at the time that the average size of tumors reached 100 $mm^3$. The leflunomide treatment was given daily. Tumor size was measured by a digital caliper and tumor volume was calculated as volume=(the longest diameter of tumor/2)*(the shortest diameter of tumor). FIG. 4B shows that 1 million MC38 cells were subcutaneously injected to $C_{57}$BL/6 mice (n=4 per each cohort). Intraperitoneal leflunomide injection and oral β-GPA administration were started at the time that the average size of tumors reached 100 $mm^3$. Leflunomide and β-GPA were given daily. As shown in FIGS. 4A and 4B, leflunomide/β-GPA combo treatment significantly reduced the growth of MC38 tumor (p=0.0004, Student t-test).

FIG. 4C shows that 1 million HS746T cells were subcutaneously injected to NOD. Cg-Prkdc$^{scid}$ Il2rg$^{tm1Wjl}$/SzJ (Nod-Scid-Gamma; NSG) mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of HS746T tumor (p=0.0045, Student t-test). Pyrimidine precursor nucleoside, uridine administration rescued the leflunomide-induced tumor growth reduction supporting the on-target efficacy of leflunomide. FIG. 4D shows that 1 million KPC LM2 cells were subcutaneously injected to $C_{57}$BL/6 mice (n=4 per each cohort). Intraperitoneal leflunomide injection and oral β-GPA administration were started at the time that the average size of tumors reached to 100 $mm^3$. Leflunomide and β-GPA were given daily. As shown in FIGS. 4C and 4D, Leflunomide/β-GPA combo treatment significantly reduced the growth of KPC LM2 tumor (p<0.0001, Student t-test).

Figures 5A, 5B:
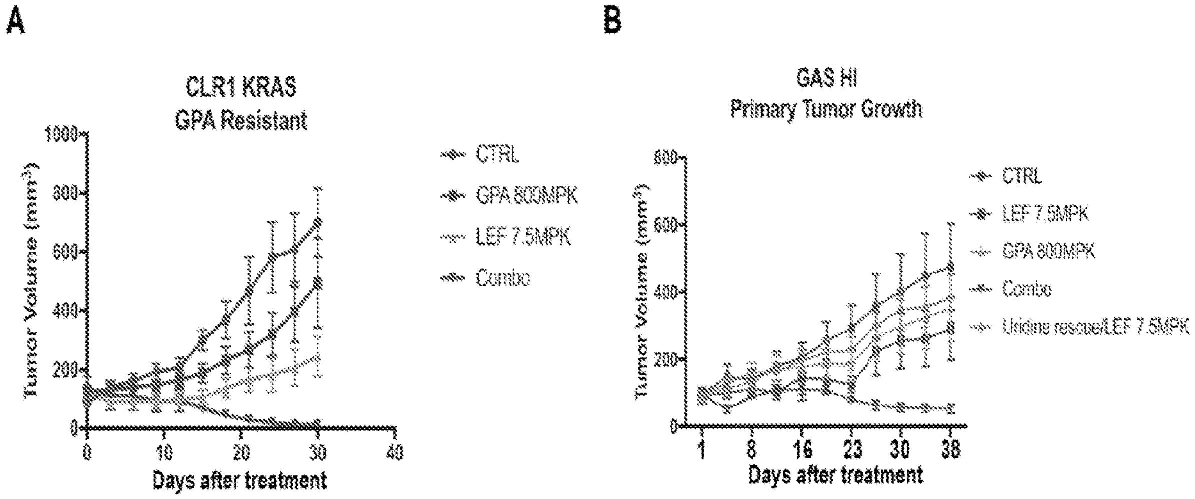
FIGS. 5A and 5B (collectively "FIG. 5") are a set of diagrams demonstrating the combinational therapeutic targeting of DHODH and SLC6a8 suppresses two independent human patient-derived tumor growth.

FIGS. 5A and 5B further demonstrated the combinational therapeutic targeting of DHODH and SLC6a8 suppressed two independent human patient-derived tumor growth. FIG. 5A shows that 30 $mm^3$ fragments of the patient-derived tumor were surgically sutured into the subcutaneous tissue of athymic nude mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of CLR1 tumor (p=0.0011, Student t-test). FIG. 5B shows that 30 $mm^3$ fragments of patient-derived tumors were surgically sutured into the subcutaneous tissue of athymic nude mice (n=4 per each cohort). Intraperitoneal leflunomide injection and oral β-GPA administration were started at the time that the average size of tumors reached 100 $mm^3$. Leflunomide and β-GPA were given daily. Leflunomide/β-GPA combo treatment significantly reduced the growth of GAS HI tumor (p=0.008, Student t-test). As shown in FIGS. 5A and 5B, Uridine administration rescued the leflunomide induced tumor growth suppression.

Discussion

Most patient-derived xenograft models consist of subcutaneous tumor tissue implantation. It was found that successful subcutaneous tumor engraftment associated with worse patient survival in those with colorectal cancer. However, among those tumors in the present study that did engraft subcutaneously, the subcutaneous tumor growth rate did not significantly correlate with patient survival. In contrast, liver metastasis growth rate was significantly correlated with patient survival. The reason for this discrepancy in the prognostic power of subcutaneous tumor growth versus liver metastatic growth is likely the greater selective pressure inherent to the liver microenvironment. Thus, the clinically predictive colorectal cancer liver metastatic PDX models described in this disclosure represents a valuable resource for the cancer community.

PCK1 is the rate-limiting enzyme in gluconeogenesis and is often upregulated in patients with metabolic syndrome and diabetes mellitus. Epidemiologic data suggest that those patients with diabetes that are on metformin, a gluconeogenic-antagonist, and exhibit improved colorectal cancer clinical outcomes relative to their metformin-free counterpart. The observations as presented herein indicate one potential mechanistic basis for the sensitivity of CRC metastatic progression to inhibition of this pathway.

Metabolic rewiring in cancer has been well-established to provide tumor cells with the necessary nutrients and anabolic components to sustain proliferative and energetic demands. While numerous pathways are involved in metabolic reprogramming, metabolic shunting into pathways including glucose metabolism, the citric acid (TCA) cycle, and lipogenesis largely support macromolecule synthesis for cancer cells. In line with these notions, there have been two reports on PCK1 and its role in cancer. Li et al. found that PCK1 enhanced melanoma tumor re-initiation (Y. Li, et al. *Cancer Res* 75, 1191-1196 (2015)). Li et al. demonstrated that, in tissue culture, melanoma 'tumor re-initiating cells' (TRC) consumed more glucose and produced more lactate and glycerate-3-phosphate; PCK1 silencing elicited the opposite phenotype in culture. Using cell culture metabolomics, Montal et al. recently described a mechanism by which PCK1 promotes colorectal cancer growth through its increased ability to metabolize glutamine into lipids and ribose (E. D. Montal, et al. *Mol Cell* 60, 571-583 (2015)). PCK1 silencing in a colorectal cancer cell line in vitro was shown to decrease glutamine utilization and TCA cycle flux. They further found that cells with increased expression of PCK1 consumed more glucose and produced more lactate. The authors performed PCK1 staining on a primary colorectal cancer tissue microarray, finding that PCK1 was overexpressed in many primary CRC biopsies, but PCK1 expression was not associated with tumor grade.

The present disclosure, however, demonstrates a major role for PCK1 in liver metastatic colonization by CRC. While it was not determined that PCK2 upregulation occurs in the mCRC model, three recent studies demonstrated that PCK2 upregulation in lung cancer cells in vitro can enhance cancer cell survival in glucose-depleted conditions (K. Leithner, et al. *Oncogene* 34, 1044-1050 (2015); E. E. Vincent, et al. *Mol Cell* 60, 195-207 (2015)). Vincent et al. found that in glucose-depleted conditions, lung cancer cells increased consumption of glutamine as an energy source in a PCK2-dependent manner. Zhao et al. observed PCK2 upregulation in tumor-initiating cells (TIC) and demonstrated that PCK2 promoted tumor initiation through reducing TCA cycle flux by lowering Acetyl-CoA (J. Zhao, et al. *Oncotarget* 8, 83602-83618 (2017)).

The present disclosure provides for three novel insights underlying the role of PCK1 in cancer progression. First, the was demonstrated that increased PCK1 strongly drives liver metastatic colonization relative to primary tumor growth. Second, it provides the first reported evidence that PCK1 can promote hypoxic survival. Third, it uncovered a key role for PCK1 and gluconeogenesis in pyrimidine biosynthesis under hypoxia. As disclosed herein, PCK1 and PCK2 support important roles for these gluconeogenesis enzymes in cancer initiation, progression, and potential novel therapies.

Because metabolic programs are altered within tumor cells in the tumor microenvironment, metabolic liabilities emerge that provide therapeutic opportunities. Past research by White et al. implicated DHODH as a regulator of melanoma formation via its effects on transcriptional elongation (R. M. White, et al. *Nature* 471, 518-522 (2011)). More recent work has implicated DHODH as a regulator of differentiation in certain myeloid leukemias and pancreatic adenocarcinoma (D. B. Sykes, et al. *Cell* 167, 171-186 e115 (2016)). Furthermore, Bajzikova et al. found that de-novo pyrimidine biosynthesis is essential for mouse breast cancer tumorigenesis in a DHODH dependent manner (M. Bajzikova, et al. *Cell Metab* 29, 399-416 e310 (2019)). The present disclosure reveals that beyond effects on cell growth in vitro and primary tumor growth, CRC metastatic progression selects for upregulation of pyrimidine biosynthesis. Moreover, the use of leflunomide to therapeutically target DHODH has been implicated under various cancer contexts as a metabolic inhibitor. As disclosed herein, it was observed that molecular or pharmacological inhibition with leflunomide of this pathway strongly impairs CRC metastatic colonization relative to primary tumor growth. The present disclosure also demonstrated that hypoxia enhanced the sensitivity of cells to DHODH inhibition, suggesting that enhanced pyrimidine biosynthesis enables enhanced growth upon hypoxia—a key feature of the hepatic tumor microenvironment.

5-Fluorouracil (5-FU) was the first chemotherapeutic to demonstrate efficacy in reducing the risk of CRC recurrence (C. G. Moertel, et al. *N Engl J Med* 322, 352-358 (1990)). This agent remains the backbone of the current FOLFOX regimen, which is administered to patients after surgical resection to reduce the risk of metastatic relapse. Interestingly, 5-FU targets thymidylate synthase, an enzyme downstream of DHODH in the pyrimidine biosynthetic pathway—supporting the premise of the dependence of and susceptibility to inhibition of this pathway in CRC metastasis. Despite its activity, a large fraction of patients treated with 5-FU nonetheless relapse. Multiple mechanisms of resistance to 5-FU have been described (C. Holohan, et al. *Nat Rev Cancer* 13, 714-726 (2013)).

As disclosed herein, inhibition of DHODH can suppress metastatic progression of a CRC cell line that is resistant to 5-FU—revealing promise for clinical testing of this agent in patients at high risk for relapse and whose tumors may exhibit resistance to 5-FU. The disclosure further demonstrated that (i) PDX modeling of CRC can be predictive of clinical survival outcomes; (ii) integration of PDX modeling with in vivo selection can give rise to highly metastatic PDX derivatives which can be profiled transcriptomically and metabolically to identify key drivers of metastatic progression; and (iii) PCK1 and DHODH represent key metabolic drivers of CRC metastasis and therapeutic targets in CRC.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A method for treating a metastatic gastrointestinal cancer in a subject in need thereof, the method comprising administering to the subject an effective amount of a dihydroorotate dehydrogenase (DHODH) inhibitor, or a pharmaceutically acceptable salt thereof, and an effective amount of a beta-guanidinopropionic acid (β-GPA), or a pharmaceutically acceptable salt thereof, to suppress metastatic colonization of gastrointestinal cancer.

2. The method of claim 1, wherein the DHODH inhibitor is selected from the group consisting of atovaquone, sodium salt of DuP-785, leflunomide, teriflunomide, BAY-2402234, AG-636, and a combination thereof.

3. The method of claim 1, wherein the administration to the subject is performed intratumorally, intravenously, subcutaneously, intraosseously, orally, transdermally, in sustained release, in controlled release, in delayed release, as a suppository, or sublingually.

4. The method of claim 1, wherein the administration to the subject is performed orally.

5. The method of claim 1, wherein the administration to the subject is performed once, twice, three, or four times per day, or as needed.

6. The method of claim 1, wherein the DHODH inhibitor or the pharmaceutically acceptable salt thereof is administered to the subject before, after, or concurrently with the β-GPA or the pharmaceutically acceptable salt thereof.

7. The method of claim 1, wherein the DHODH inhibitor or the pharmaceutically acceptable salt thereof and the β-GPA or the pharmaceutically acceptable salt thereof are provided in a single composition.

8. The method of claim 1, wherein the DHODH inhibitor or the pharmaceutically acceptable salt thereof and the β-GPA or the pharmaceutically acceptable salt thereof are provided in two separate compositions.

9. The method of claim 1, further comprising administering to the subject an additional therapeutic agent.

10. The method of claim 9, wherein the additional therapeutic agent is an anti-cancer agent or an anti-tumor agent.

11. The method of claim 1, wherein the cancer is colorectal cancer, gastric cancer, or pancreatic cancer.

12. The method of claim 1, wherein the cancer is cholangial cancer.

13. The method of claim 1, wherein the method suppresses metastatic colonization of cancer in the liver of a subject in need thereof.

14. The method of claim 1, wherein the subject is a mammal.

15. The method of claim 14, wherein the mammal is human.

16. A method for treating a gastrointestinal cancer in a subject in need thereof, comprising administering to the subject an effective amount of a DHODH inhibitor, or a pharmaceutically acceptable salt thereof, and β-GPA, or a pharmaceutically acceptable salt thereof in amounts which together are effective to suppress metastatic progression of the cancer.

17. The method of claim 16, wherein the DHODH inhibitor, or a pharmaceutically acceptable salt thereof, and β-GPA, or a pharmaceutically acceptable salt thereof are administered in amounts that together are effective to suppress metastatic colonization of the cancer.

18. The method of claim 16, wherein the DHODH inhibitor, or a pharmaceutically acceptable salt thereof, and β-GPA, or a pharmaceutically acceptable salt thereof are administered in amounts that together are effective to suppress metastatic colonization of the cancer to the liver and/or brain.

19. The method of claim 16, wherein the DHODH inhibitor, or a pharmaceutically acceptable salt thereof, is atovaquone, sodium salt of DuP-785, leflunomide, teriflunomide, BAY-2402234, AG-636, or a combination thereof.

20. The method of claim 19, wherein the DHODH inhibitor, or a pharmaceutically acceptable salt thereof, is leflunomide.

21. The method of claim 16, wherein the cancer is colorectal cancer, pancreatic cancer, or liver cancer.

22. The method of claim 16, wherein the gastrointestinal cancer is colorectal cancer, esophageal cancer, or gastric cancer.

23. The method of claim 16, wherein the method further comprises administering to the subject an additional anti-cancer therapy.

24. The method of claim 23, wherein the additional anti-cancer therapy comprises surgery, radiation therapy, or one or more therapeutic agents, or a combination thereof.

25. The method of claim 24, wherein the one or more therapeutic agents comprises irinotecan, oxaliplatin, cetuximab, bevacizumab, leucovorin, or 5-fluorouracil, or a combination thereof.

26. The method of claim 16, wherein the subject has previously been administered at least one prior anti-cancer therapy.

27. The method of claim 26, wherein the at least one prior anti-cancer therapy comprises surgery, radiation therapy, or one or more therapeutic agents, or a combination thereof.

28. The method of claim 16, wherein the cancer expresses creatine kinase brain-type (CKB).

29. The method of claim 16, wherein the cancer has been determined to express CKB based on histological examination of a tissue sample from the subject.

30. The method of claim 16, wherein the cancer expresses SLC6a8.

31. The method of claim 16, wherein the cancer has been determined to express SLC6a8 based on histological examination of a tissue sample from the subject.

32. The method of claim 31, wherein the subject has been identified as likely to respond to treatment with a DHODH inhibitor and β-GPA, or a pharmaceutically acceptable salt thereof based on expression of CKB and/or SLC6a8 determined from histological examination of a tissue sample from the subject.

* * * * *